(12) United States Patent  
Bailon et al.

(10) Patent No.: US 7,084,261 B2  
(45) Date of Patent: Aug. 1, 2006

(54) PEGYLATED T1249 POLYPEPTIDE

(75) Inventors: Pascal S. Bailon, Florham Park, NJ (US); Chee-Youb Won, Livingston, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 4 days.

(21) Appl. No.: 10/625,103

(22) Filed: Jul. 22, 2003

(65) Prior Publication Data

US 2004/0171542 A1 Sep. 2, 2004

Related U.S. Application Data

(60) Provisional application No. 60/439,213, filed on Jan. 10, 2003, provisional application No. 60/398,190, filed on Jul. 24, 2002.

(51) Int. Cl.
*A61K 38/12* (2006.01)
*C08H 1/00* (2006.01)

(52) U.S. Cl. ........................ 530/402; 530/324

(58) Field of Classification Search .................. 514/12
See application file for complete search history.

(56) References Cited

U.S. PATENT DOCUMENTS

| | | | |
|---|---|---|---|
| 5,252,714 A | 10/1993 | Harris et al. | |
| 5,464,933 A | 11/1995 | Bolognesi et al. | |
| 5,672,662 A | 9/1997 | Harris et al. | |
| 5,795,569 A * | 8/1998 | Bartley et al. | ............. 424/85.1 |
| 5,955,422 A | 9/1999 | Lin | |
| 5,959,265 A | 9/1999 | Van Ligten | |
| 5,990,237 A | 11/1999 | Bentley et al. | |
| 6,015,881 A | 1/2000 | Kang et al. | |
| 6,258,787 B1 | 7/2001 | Isner | |
| 6,340,742 B1 | 1/2002 | Burg et al. | |
| 6,348,568 B1 | 2/2002 | Barney et al. | |
| 2003/0125516 A1 * | 7/2003 | Bray et al. | ................... 530/324 |

OTHER PUBLICATIONS

Reddy, K.R., Controlled-Release, Pegylation, Liposomal Formulations: New Mechanism in the Delivery of Injectable Drugs (2000), vol. 34, pp. 915-923.*

Contrled-Release, Pegylation, Liposomal Formulations: New Mechanism in the Delivery of Injectable Drugs (2000), vol. 34, pp. 915-923.

Biomaterials 22, p. 405-417 (2001) "Review-Peptide and protein PEGylation. . . ".

Chem. Soc. vol. 85, p. 2149 (1963).

Sheppard, R.C. et al., J. Chem. Soc. Chem. Comm. 165-166 (1985).

* cited by examiner

*Primary Examiner*—Bruce R. Campbell
*Assistant Examiner*—Thomas S. Heard
(74) *Attorney, Agent, or Firm*—George W. Johnston; Dennis P. Tramaloni; Samuel H. Megerditchian

(57) ABSTRACT

Pegylated T1249 polypeptide compounds are provided. Also provided are pharmaceutical compositions containing pegylated T1249 polypeptide compounds, and methods of making. Further provided are methods of inhibiting HIV infection using such compounds and compositions.

149 Claims, 7 Drawing Sheets

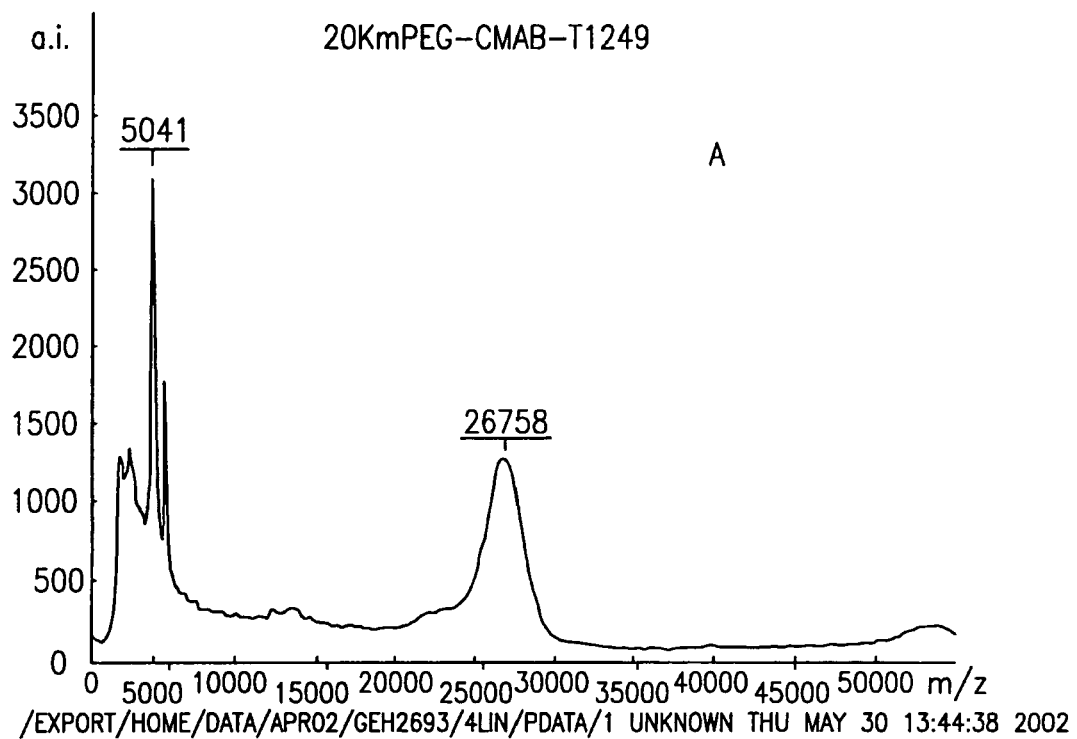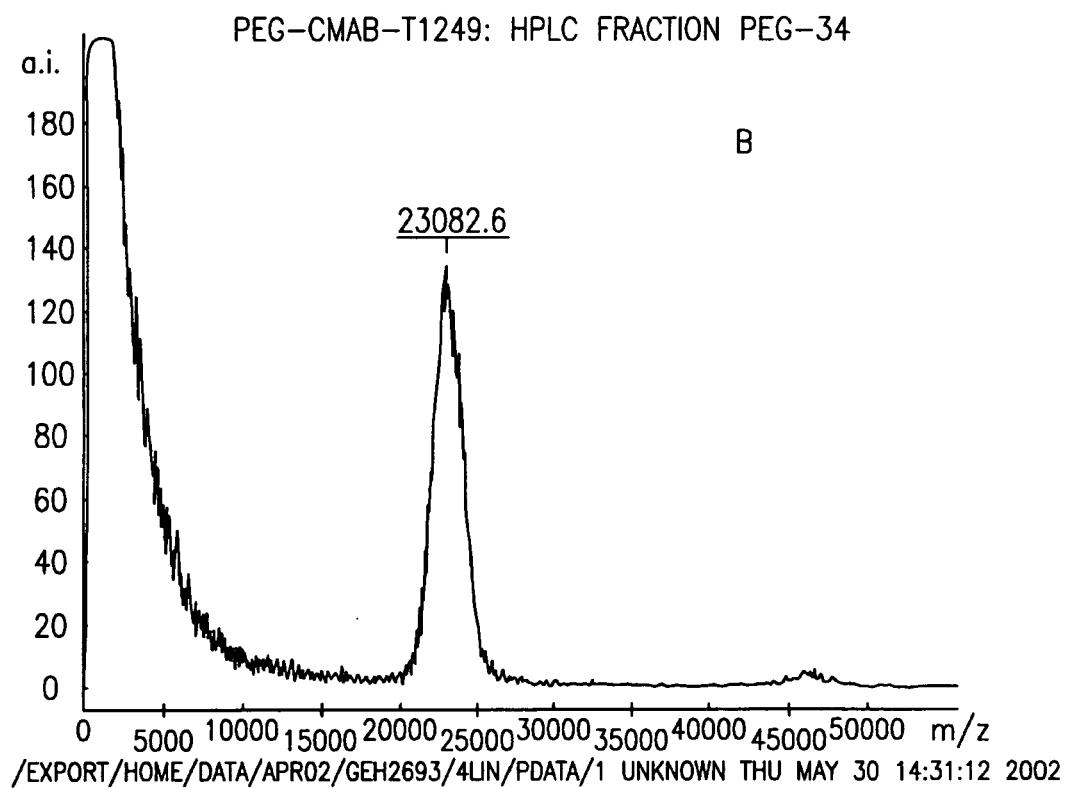
FIG. 2

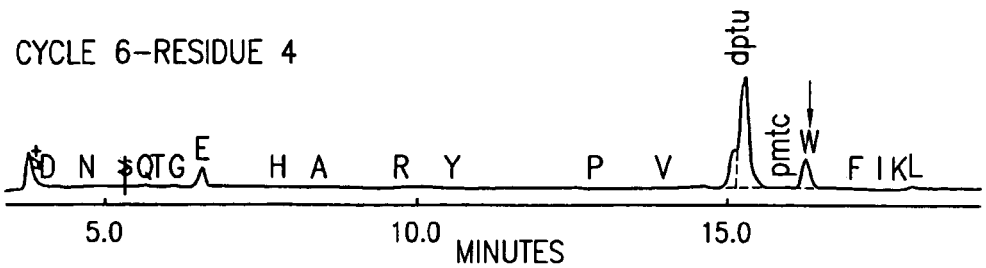
CYCLE 6-RESIDUE 4
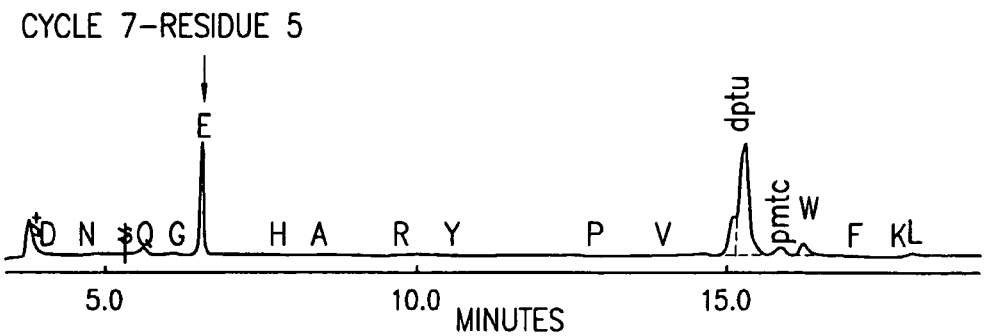
CYCLE 7-RESIDUE 5
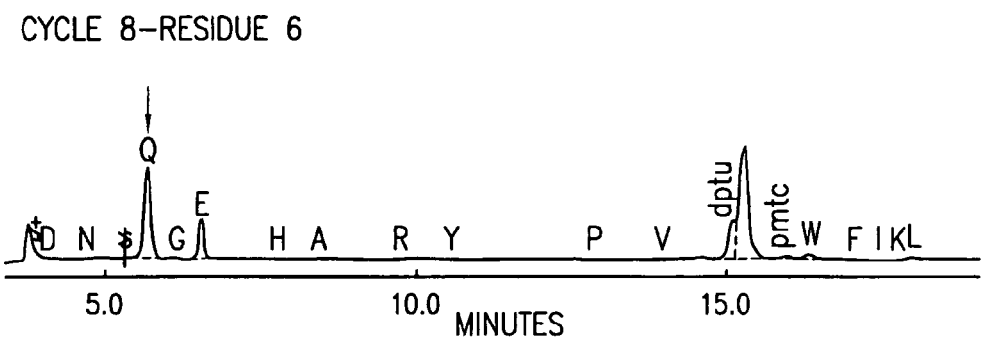
CYCLE 8-RESIDUE 6
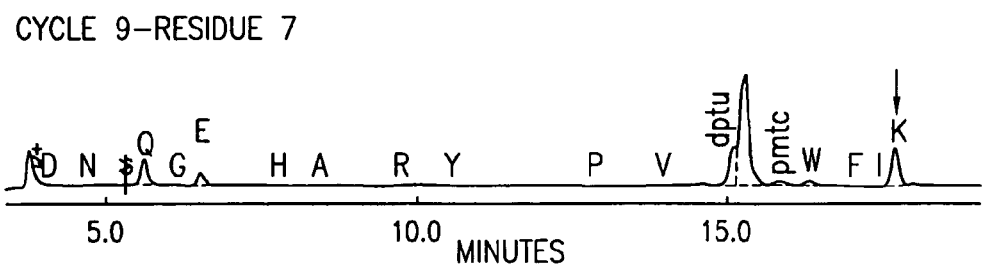
CYCLE 9-RESIDUE 7
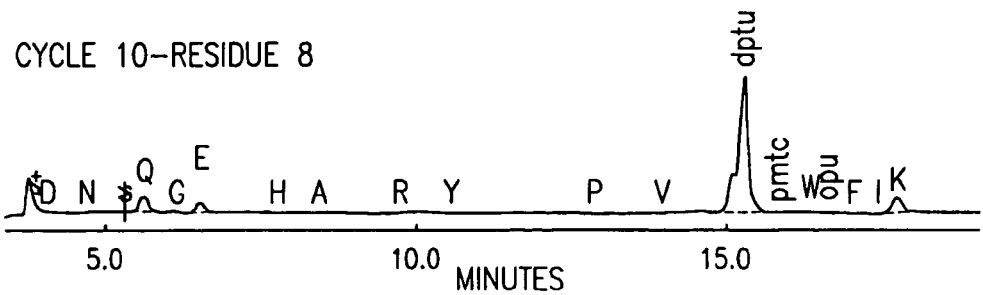
CYCLE 10-RESIDUE 8
*FIG. 3A*

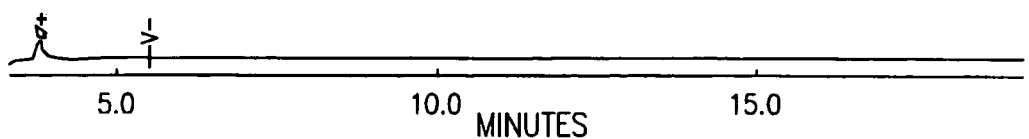
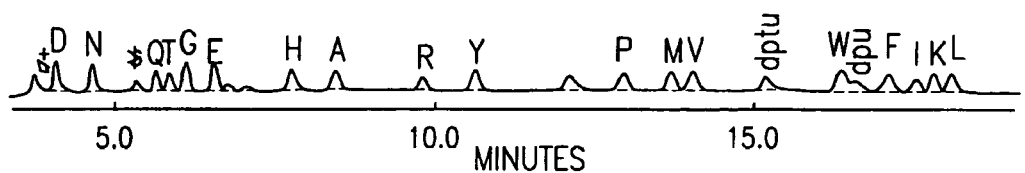
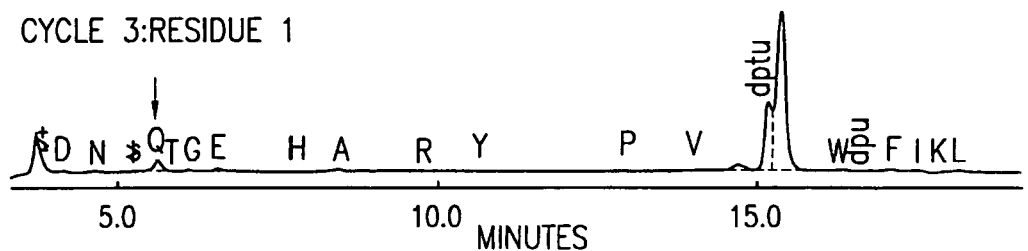
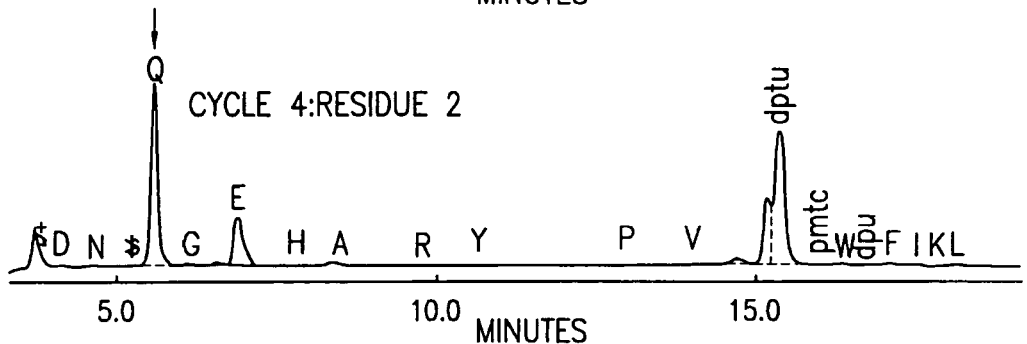
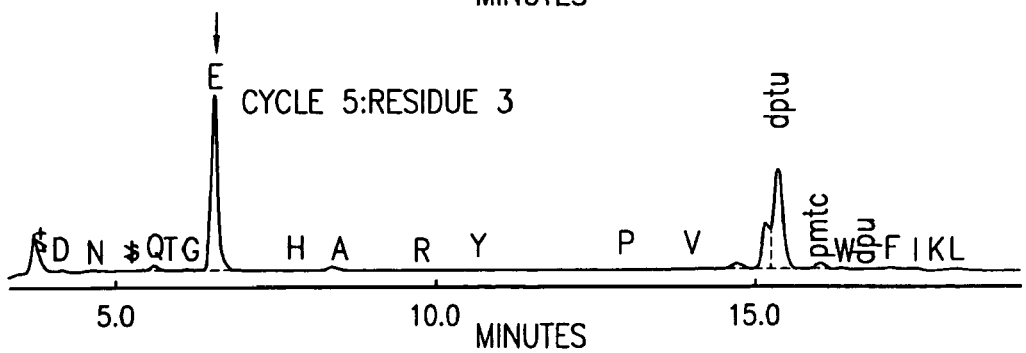
FIG. 3B

PEGYLATED T1249 POLYPEPTIDE

PRIORITY TO PROVISIONAL APPLICATIONS

This application claims priority to prior provisional applications Ser. No.: 60/439,213, filed on Jan. 10, 2003, and Ser. No.: 60/398,190, filed on Jul. 24, 2002.

FIELD OF THE INVENTION

The present invention relates to pegylated T1249 polypeptide compounds, and to related methods of using and making such compounds, such as in pharmaceutical compositions and therapeutic methods of treatment.

BACKGROUND OF THE INVENTION

Some viruses, especially HIV, must undergo a complex process called fusion in order to enter the host cell and reproduce. During fusion, the outer membrane of the virus fuses with the membrane of the host cell. In the case of HIV, the outer membrane of the HIV virus fuses with the membrane of the CD4+ T cell during reproduction.

T1249 is a member of a new class of antiviral agents that inhibit virus/membrane fusion. In the case of HIV, this provides two salutary effects:

the reproduction of HIV is blocked and resultant death of the CD4+ T cells does not occur.

Viral resistance to currently approved anti-HIV drugs is a significant issue in the clinical management of HIV today. Many patients who begin combination antiretroviral treatment with currently approved medications will develop resistance to one or more of these agents over time. Research suggests, however, that T1249 may be unaffected by resistance to any of the currently approved antiretroviral classes. (Data presented at the 5th International Workshop on Drug Resistance and Treatment Strategies in Scottsdale, Ariz., Jun. 4–8, 2001).

An analysis of T1249 dose-ranging in a clinical trial suggests that daily dose of T1249, and not prior antiretroviral treatment experience, including mutations to all approved classes of HIV drugs, is the only variable that is associated with the viral load reduction among treatment-experienced, patients. Additional experiments show that the in vitro activity of T1249 is not affected by mutations associated with resistance to reverse transcriptase inhibitors and protease inhibitors.

Like many polypeptide therapeutic agents, T1249 is generally administered by injection. Current therapeutic protocols often involve more than one daily injection.

It would, therefore, be advantageous to provide T1249 polypeptides and pharmaceutical compositions having improved performance and pharmacokinetic characteristics. It would be particularly advantageous to provide for lower therapeutic doses of T1249, less frequent administrations, and/or extended duration of action.

These and other objects of the present invention are described in greater detail below.

SUMMARY OF THE INVENTION

The present invention provides a compound of formula:

wherein $R_1$ is a capping group, m is from 1 to 17, n is from 10 to 1,000, p is from 1 to 3, and NHT1249 is a T1249 polypeptide covalently bonded through its terminal α-amino group.

In one embodiment of the compound of the present invention $R_1$ is methoxy, m is 1, n is from 100 to 750, and p is 3.

Also provided is a pharmaceutical composition comprising, in admixture with a pharmaceutically acceptable excipient, a compound of formula (I), wherein $R_1$, m, n, p, and NHT1249 are defined as above.

In one embodiment of the pharmaceutical composition of the present invention $R_1$ is methoxy, m is 1, n is from 100 to 750, and p is 3.

The present invention further provides a method of inhibiting HIV infection comprising administering a pharmaceutical composition comprising, in admixture with a pharmaceutically acceptable excipient, a compound of formula (I), wherein $R_1$, m, n, p, and NHT1249 are defined as above.

In one embodiment of the method of inhibiting HIV infection $R_1$ is methoxy, m is 1, n is from 100 to 750, and p is 3.

Further provided is a method for making a pegylated T1249 polypeptide comprising reacting a T1249 polypeptide with a polyethylene glycol aldehyde of formula:

wherein $R_1$, m, n, n, and p are defined as above; to produce a compound of formula (I), wherein the polyethylene glycol aldehyde molecule is bonded to the N-terminal amino group of the T1249 polypeptide.

BRIEF DESCRIPTION OF THE DRAWINGS

FIG. 2 shows a matrix assisted laser desorption ionization time of flight (MALDI TOF) mass spectrum of the collected HPLC fraction PEG-34 (FIG. 1). Spectra were acquired in linear mode with trans-3-indoleacrylic acid as the matrix.

FIG. 3 shows N-terminal (Edman) sequencing of the collected HPLC fraction PEG-34 (FIG. 1).

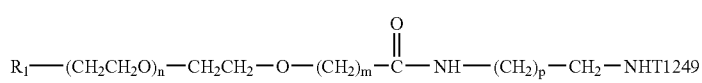

Figure 6:
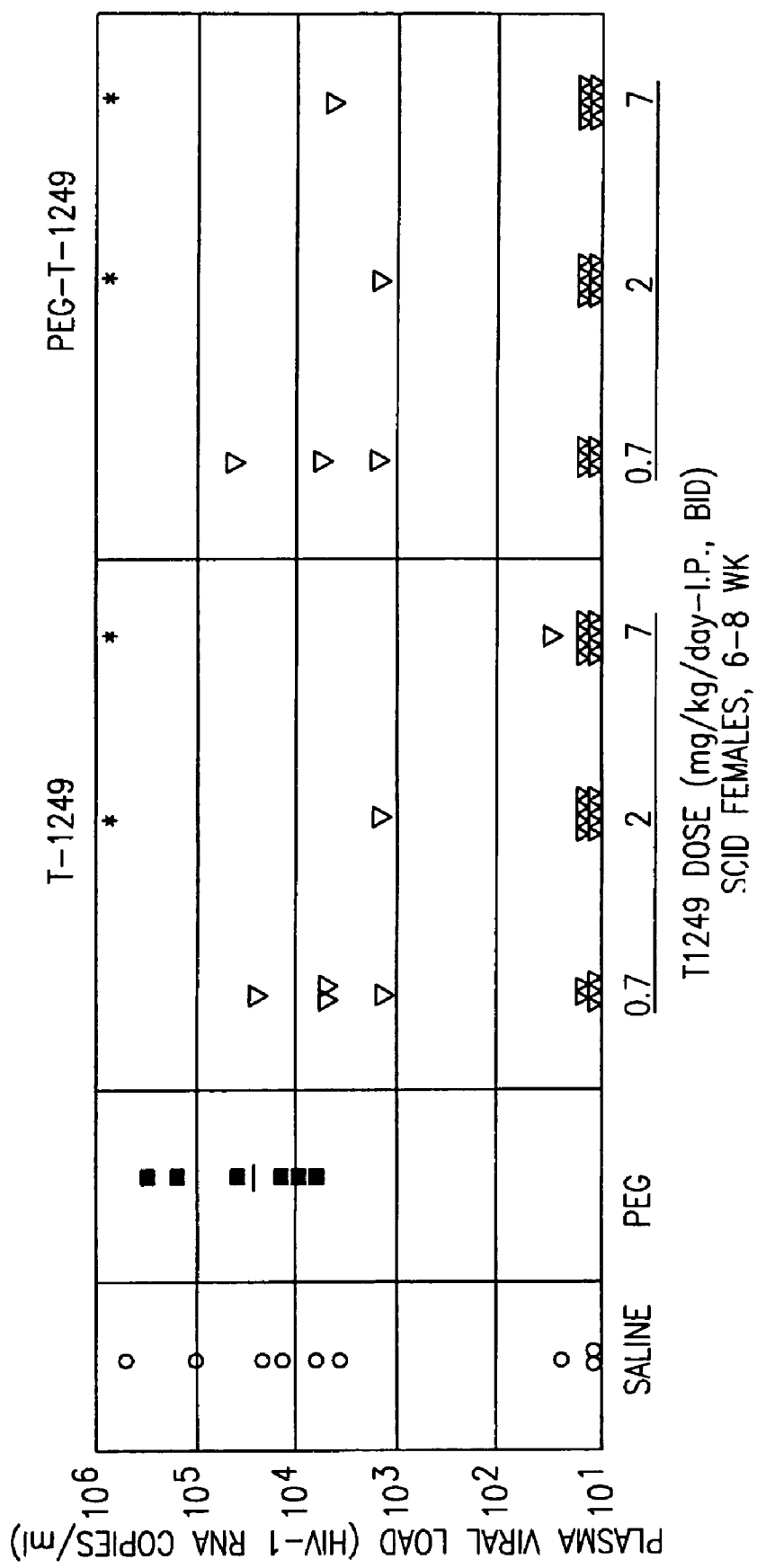

FIG. 6 shows the effect of T1249 and mPEG$_{20k}$-CMAB-T1249 dosing on the HIV-1 viral load in SCID mice.

DETAILED DESCRIPTION OF THE INVENTION

As noted above, T1249 is a "fusion inhibitor" polypeptide. T1249 consists of 39 amino acids. The polypeptide sequence of T1249 is:

[SEQ. ID. NO:1]
WQEWEQKITALLEQAQIQQEKNEYELQKLDKWASLWEWF

The N-terminus (or amino terminus) amino acid is tryptophane (W). The C-terminus (or carboxy terminus) amino acid is phenylalanine (F).

As described in Table 1 of U.S. Pat. No. 6,348,568 (Seq. ID No. 1071), which is hereby incorporated by reference in its entirety, the T1249 polypeptide sequence may be blocked/derivatized at one or both of its amino and carboxy termini. As described in U.S. Pat. No. 6,348,568, the tryptophane amino terminus is blocked/derivatized with an acyl group and the phenylalanine carboxy-terminus is blocked/derivatized with an amino group (the latter resulting in a conversion of the —COOH→—CONH$_2$).

As used herein, "T1249" shall be understood to mean [SEQ.ID.NO:1], optionally blocked at the phenylalanine C-terminus with an amino group. In other words, when reference is made to "T1249," the phenylalanine C-terminus is either —COOH or —CONH$_2$.

The present invention provides pegylated T1249 compounds of the following formula:

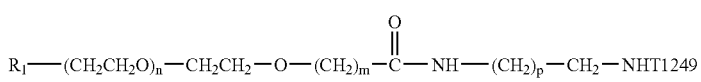

(I)

wherein
R$_1$ is a capping group,
m is from 1 to 17,
n is from 10 to 1,000,
p is from 1 to 3, and
NHT1249 is a T1249 polypeptide covalently bonded through its terminal α-amino group.

As used herein the R$_1$ "capping group" is any suitable chemical group which, depending upon preference, is generally unreactive or generally reactive with other chemical moieties. In the above compound the polyethylene glycol is covalently bonded to the α-amino group of T1249. The R$_1$ capping group is selected to permit or prevent bifunctionality, e.g., covalent attachment to a second chemical moiety of interest.

In the case that the capping group is generally unreactive with other chemical moieties, R$_1$ is relatively inert and therefore will not covalently bond with another chemical moiety. Suitable generally unreactive R$_1$ capping groups include: hydrogen, hydroxyl, lower alkyl, lower alkoxy, lower cycloalkyl, lower alkenyl, lower cycloalkenyl, aryl, and heteroaryl.

As used herein, the term "lower alkyl" means a straight-chain or branched-chain alkyl group containing from 1 to 7, preferably from 1 to 4, carbon atoms, such as methyl, ethyl, n-propyl, isopropyl, n-butyl, sec.butyl, tert.butyl, n-pentyl, n-hexyl, n-heptyl and the like. The "lower alkyl" is optionally substituted with one or more groups independently selected from halogen, lower alkyl, lower alkoxy, lower cycloalkyl, lower alkenyl, lower cycloalkenyl, aryl, and heteroaryl.

The term "lower alkoxy" means a lower alkyl group as defined earlier which is bonded via an oxygen atom, with examples of lower alkoxy groups being methoxy, ethoxy, n-propoxy, isopropoxy, n-butoxy, sec.butoxy, tert.butoxy, n-pentoxy and the like. The "lower alkoxy" is optionally substituted with one or more groups independently selected from halogen, lower alkyl, lower alkoxy, lower cycloalkyl, lower alkenyl, lower cycloalkenyl, aryl, and heteroaryl.

The term "lower cycloalkyl" means cycloalkyl group containing from 3 to 7, preferably from 4 to 6, carbon atoms, i.e., cyclopropyl, cyclobutyl, cyclopentyl, cyclohexyl or cycloheptyl. The "lower cycloalkyl" is optionally substituted with one or more groups independently selected from halogen, lower alkyl, lower alkoxy, lower cycloalkyl, lower alkenyl, lower cycloalkenyl, aryl, and heteroaryl.

As used herein, the term "lower alkenyl" means straight-chain or branched-chain alkenyl group containing from 2 to 7, preferably from 2 to 5, carbon atoms, e.g., ethenyl, butenyl, pentenyl, hexenyl and the like. The "lower alkenyl" is optionally substituted with one or more groups independently selected from halogen, lower alkyl; lower alkoxy, lower cycloalkyl, lower alkenyl, lower cycloalkenyl, aryl, and heteroaryl.

The term "lower cycloalkenyl" means a cycloalkenyl group containing from 4 to 7 carbon atoms, e.g., cyclobutenyl, cyclopentenyl, cyclohexenyl and the like. The "lower cycloalkenyl" is optionally substituted with one or more groups independently selected from halogen, lower alkyl, lower alkoxy, lower cycloalkyl, lower alkenyl, lower cycloalkenyl, aryl, and heteroaryl.

The term "aryl" means a phenyl or naphthyl group which is unsubstituted or optionally mono- or multiple-substituted by halogen, lower alkyl, lower alkoxy, trifluoromethyl, hydroxyl, carboxylic acid, carboxylic ester, nitro, amino, or phenyl, particularly by halogen, lower alkyl, lower alkoxy, trifluoromethyl, hydroxyl, nitro, amino and phenyl.

The term "heteroaryl" means a 5- or 6-membered heteroaromatic group which contains one or more hetero atoms selected from N, S, and O and which may be benz-fused and/or substituted in the same manner as "aryl" defined earlier.

Preferred generally unreactive R$_1$ capping groups include methoxy, hydroxy, or benzyloxy. An especially preferred, R$_1$ capping group is methoxy. When R$_1$ is methoxy the pegylated polypeptide compounds are sometimes referred to herein, in part, as "mPEG" compounds, wherein the "m" stands for methoxy.

If the R$_1$ capping group is generally reactive with other chemical moieties, then R$_1$ is a functional group capable of reacting with some functional group, such as an amine and/or sulfhydryl in a peptide and/or protein. In such a case, R$_1$ may be a functional group that is capable of reacting readily with electrophilic or nucleophilic groups on other molecules, in contrast to those groups that require strong catalysts or highly impractical reaction conditions in order to react. If $R_1$ is relatively reactive, the polyethylene glycol aldehyde may covalently bond with another chemical moiety.

Examples of suitable generally reactive $R_1$ capping groups include: halogen, epoxide, maleimide, orthopyridyl disulfide, tosylate, isocyanate, hydrazine hydrate, cyanuric halide, N-succinimidyloxy, sulfo-N-succinimidyloxy, 1-benzotriazolyloxy, 1-imidazolyloxy, p-nitrophenyloxy, and

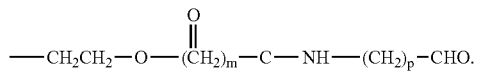

The term "halogen" means fluorine, chlorine, bromine, or iodine. A preferred generally reactive $R_1$ capping group is

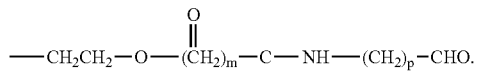

When this $R_1$ capping group is present, it will be appreciated that in the compounds of the present invention the first m, n, and/or p may be the same or different from the second m, n, and/or p in the formula. It is preferred, however, that both m's have the same value, both n's have the same value, and both the p's have the same value.

In the present invention, m is from 1 to 17. In a preferred embodiment, m is from 1 to 14. More preferably m is from 1 to 7, and even more preferably, m is from 1 to 4. Most preferably, m is 1.

In the present invention, n is from 10 to 1,000. In a preferred embodiment of the present invention n is from 20 to 1,000. Preferably, n is from 50 to 1,000, even more preferably n is from 75 to 1,000. Most preferably, n is from 100 to 750.

In the present invention, p is from 1 to 3. Preferably, p is 3.

In preferred embodiments, p is 3, $R_1$ is methoxy, m is 1, and n is from 100 to 750; or p is 2, $R_1$ is methoxy, m is 1, and n is from 100 to 750; or p is 1, $R_1$ is methoxy, m is 1, and n is from 100 to 750.

The present invention provides embodiments of formula (I), wherein $R_1$ is methoxy, m is 1, n is from 100 to 750, p is 3, and NHT1249 is a T1249 polypeptide covalently bonded through its terminal α-amino group.

As noted above, the pegylated T1249 compounds of the invention covalently link the α-amino group of T1249 to a polyethylene glycol derivative having a particular structure. These pegylated compounds may be made in any manner desired, but generally they are prepared by reacting T1249 with separately prepared polyethylene glycol derivatives. For example, the T1249 polypeptide may be pegylated by blocking all lysine residues and reacting this blocked T1249 with a polyethylene glycol derivative. The blocked lysine residues of the T1249 polypeptide are then deblocked, resulting in a terminally pegylated T1249.

The T1249 polypeptide may be prepared in any suitable manner. For example, the compounds may be synthesized using the classic Merrifield solid phase synthesis techniques involving a solid phase method employing Boc-amino acid (Chem. Soc., 85, 2149, 1963), by using manual or automated procedures, using a solid phase method employing an Fmoc-amino acid (Sheppard, R. C. et al., J. Chem. Soc. Chem. Comm., pp. 165–166 (1985)), using an Advanced Chemtech model 200 available from Advanced Chemtech., Louisville, Ky., using a Millipore 9050+ available from Millipore, Bedford Mass., or other available instrumentation.

T1249 may be produced by incorporating cDNA coding compounds of the invention into functional viral or circular plasmid DNA vectors. The vectors or plasmids can be used to transfect or transform selected microorganisms. The transformed or transfected microorganisms can be cultured under conditions that are conducive to express vector-borne DNA sequences and isolation of the desired peptides from the growth medium can be achieved. (See, for example U.S. Pat. No. 5,955,422, the entirety of which is incorporated herein by reference as if recited in full.)

T1249 may also be prepared by standard recombinant DNA technology using techniques that are well known in the art. For example, the procedures outlined in Sambrook et al. *Molecular Cloning: A Laboratory Manual,* 2nd edition, (Cold Spring Harbor Press, Cold Spring Harbor, N.Y.) or Ausubel et al., *Current Protocols in Molecular Biology,* John Wiley and Sons, New York (1995), both of which are herein incorporated by reference.

A particular method for making T1249 is described in U.S. Pat. No. 6,258,7872 and U.S. Pat. No. 6,348,568, each of which is hereby incorporated by reference.

After cleavage and deprotection, T1249 may be purified by any suitable means. For example, ion exchange, gel filtration chromatography and/or a reverse-phase column/HPLC system can be used to purify full length T1249 from fragments thereof. In the case when a T1249 precursor is first prepared, with a blocking/protecting group attached to the N-terminus (e.g., acyl group) and/or the C-terminus (e.g., amino group), one or both of those groups may be removed using known techniques.

The amino acid sequence of T1249 may be confirmed and identified using standard amino acid analysis as well as manual and automated Edman degradation and determination of each amino acid. HPLC analysis and mass spectrometry may also be used to verify the production of T1249.

Polyethylene glycol aldehyde compounds which may be reacted with T1249 may also be made in any desired manner. It is preferred, however, that the polyethylene glycol be made in accordance with the methods described in U.S. patent application Ser. No. 60/398,196, filed Jul. 24, 2002, entitled "Polyethylene Glycol Aldehydes," the entirety of which is hereby incorporated by reference.

Generally, a polyethylene glycol aldehyde of the formula:

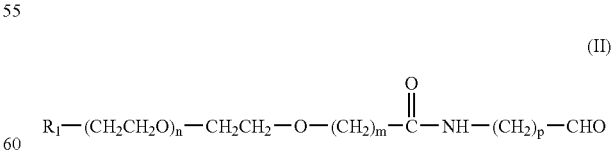

(II)

wherein $R_1$, m, n, and p are defined as above is used to pegylate the T1249. The polyethylene glycol aldehyde used to pegylated the T1249 may be prepared by any suitable means. One preferred polyethylene glycol aldehyde is prepared as follows:

Reaction Scheme for mPEG$_{10k}$-butanoaldehyde

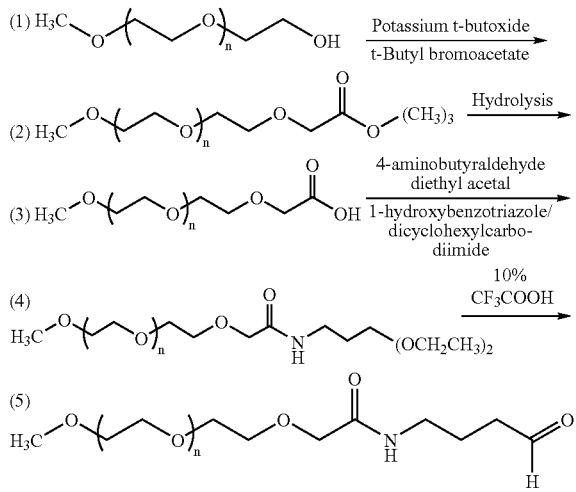

Polyethylene glycol aldehydes of varying size (e.g., varying n values) may be prepared by following the general reaction scheme above.

The pegylated T1249 compounds of the present invention may be prepared by any suitable means. Further provided by the invention, however, is a method for pegylating a T1249 polypeptide comprising reacting a T1249 polypeptide, NHT1249, with a-polyethylene glycolaldehyde of formula:

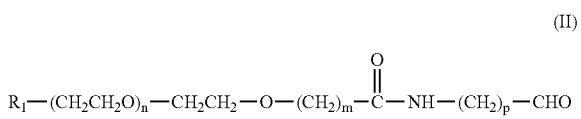

(II)

wherein $R_1$, m, n, n, and p are defined as above;

to produce a compound of formula:

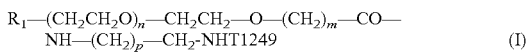

(I)

wherein the polyethylene glycol aldehyde molecule is bonded to the N-terminal amino group of the T1249 polypeptide.

The pegylated T1249 is prepared by adding T1249 and the PEG reagent in a molar ratio range of 1:1 to 1:100. The T1249 has a free α-amino group (any acyl group is removed) and either a free carboxy group or an amino-protected carboxy group, as discussed above. The reaction mixture is placed in a borate or phosphate buffer at room temperature or 4 degrees Celsius for about 0.5 to 24 hours at a pH range of 5.5 to 7.4. The molar ratio of PEG reagent to peptide/proteins is between 1:1 to 100:1. The concentration of peptide/proteins is between 1 to 10 mg/ml. The concentration of buffer is usually 10 to 500 mM.

The pegylated T1249 is purified by taking the reaction mixture of pegylated T1249 and diluting it with an equilibration buffer (20 mM Tris, pH 7.5). The resulting mixture is then applied on a Q-Sepharose column. After the mixture is applied on the QA column, it is washed with the equilibration buffer eluted with 75 M NaCl; eluted with 200 mM NaCl; eluted with 1 M NaCl; and regenerated with 1M HOAC+1M NaCl and 0.5 NaOH.

By using reverse phase HPLC, it is possible to readily separate and isolate the N-terminal, monopegylated product from other byproducts in the mixture. For example, in a chromatogram of pegylated T-1249, several peaks may form, each with different retention times. The first peak may represent unreacted peptide, at 10.7 minutes, and the second peak may represent monopegylated peptide, at 17.6 minutes, followed by di-pegylated peptide, at 19 minutes. Each collected product was confirmed by Matrix Assisted Laser Desorption/Ionization-Time of Flight Mass Spectrometry (MALDI-TOF).

In preferred embodiments of the pegylated T1249 polypeptides of the present invention, p is 3, $R_1$ is methyl, m is 1, and n is from 100 to 750; or p is 2, $R_1$ is methoxy, m is 1, and n is from 100 to 750; or p is 1, $R_1$ is methoxy, m is 1, and n is from 100 to 750.

Also provided is a pegylated T1249 polypeptide of the following formula:

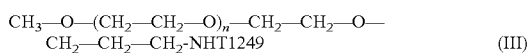

(III)

wherein n is from 10 to 1,000 and NHT1249 is a T1249 polypeptide covalently bonded through its terminal α-amino group. In one embodiment n is approximately 225, for example, 227. In another embodiment, n is approximately 450.

This pegylated T1249 polypeptide may be made in any desired manner, preferably, it is made by the method described in Example 7.

The pharmaceutical compositions of the invention comprise, in admixture with a pharmaceutically acceptable excipient, a compound of formula (I), wherein $R_1$, m, n, p, and NHT1249 are defined as above The pharmaceutical compositions of the present invention comprising pegylated T1249 polypeptides, or the salts thereof, may be manufactured in any desired manner, e.g., by means of conventional mixing, encapsulating, dissolving, granulating, emulsifying, entrapping, or lyophilizing processes. These pharmaceutical preparations may be formulated with therapeutically inert, inorganic or organic excipients and carriers. Suitable excipients for injection include water, alcohols, polyols, glycerine, vegetable oils, phospholipids and surfactants.

The pharmaceutical preparations may also contain preserving agents, solubilizing agents, stabilizing agents, wetting agents, emulsifying agents, sweetening agents, coloring agents, flavoring agents, salts for varying the osmotic pressure, buffers, coating agents, or antioxidants. They may also contain other therapeutically valuable substances, including additional active ingredients.

The formulations suitable for administration by injection (including injection intraperitoneally, intramuscularly, subcutaneously, intravenously, or by continuous infusion) may conveniently be presented in unit dosage form and may be prepared by conventional pharmaceutical techniques. Such techniques include the step of bringing into association the pegylated T1249 polypeptides and the pharmaceutical carrier(s) or excipient(s). In general, the formulations are prepared by uniformly and intimately bringing into association the pegylated T1249 polypeptides with liquid carriers. Formulations suitable for administration by injection include: aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampoules and vials, and may be stored in a freeze-dried (lyophilized) conditions requiring only-the addition of the sterile liquid carrier, for example, water for injections, immediately prior to use.

Preferred unit dosage formulations are those containing a daily dose, daily sub-dose, weekly dose, weekly sub-dose, as herein above recited, or an appropriate fraction thereof, of the administered ingredient.

Preferably, the pegylated T1249 polypeptide is in unit dosage form. As used herein, "unit dosage form," means that an amount appropriate for a single dose the pegylated T1249 polypeptide is in a premeasured and/or prepackaged form. This allows for convenient preparation of the pegylated T1249 polypeptide for administration, and may even allow for self-administration by the patient. The unit dosage amount will obviously depend on the amount of pegylated T1249 polypeptide to be delivered, and the frequency of dosing.

The pegylated T1249 polypeptide may also be provided in a lyophilized powder form in a unit dosage amount, suitable for reconstitution with a pharmaceutically acceptable excipient just prior to the time of administration.

A particular pharmaceutical composition of the invention comprises, in admixture with a pharmaceutically acceptable excipient, a compound of formula (I), wherein $R_1$ is methoxy, m is 1, n is from 100 to 750, and p is 3.

Another pharmaceutical composition of the invention is a pharmaceutical composition comprising, in admixture with a pharmaceutically acceptable excipient, a compound of formula (III), wherein n is from 10 to 1,000 and NHT1249 is a T1249 polypeptide covalently bonded through its terminal α-amino group. In one embodiment n is approximately 225, for example 227. In another embodiment, n is approximately 450.

The present invention further provides methods of inhibiting HIV infection comprising administering to a patient a pharmaceutical composition comprising, in admixture with a pharmaceutically acceptable excipient, a compound of formula (I), wherein $R_1$, m, n, p, and NHT1249 are defined as above.

The pegylated T1249 polypeptides are generally administered in the manner (unpegylated) T1249 polypeptides are presently administered. Modifications may be made, however, to take advantage of the improved pharmacokinetic properties of the pegylated T1249 polypeptides.

In the method of inhibiting HIV of the invention, the pharmaceutical composition may be administered in any suitable manner and route. In a preferred method the pegylated T1249 polypeptide is administered in the form of an injectable solution or suspension. Preferably, the injectable solution or suspension is administered by subcutaneous injection or intravenously.

In another preferred method, the pegylated T1249 polypeptide is,administered though a transdermal delivery device, e.g., a transdermal patch.

In the method of inhibiting HIV of the invention, the pharmaceutical composition may be administered in any suitable dosage and schedule. The pharmaceutical compositions of the invention can be administered in any form, and via any route, desired. Generally, however, the pegylated T1249 polypeptides of the present invention are administered parenterally, for example, in the form of injection solutions.

Determination of a therapeutically effective amount is within the skill in the art, and the therapeutically effective amount or dosage of a pegylated T1249 polypeptide according to this invention may vary and will be adjusted to the individual requirements in each particular case. In general, in the case of administration by injection to adult humans weighing approximately 70 Kg, a daily dosage of about 50 mg to about 300 mg, preferably from about 50 mg to about 200 mg, should be appropriate, although the upper limit may be exceeded when indicated. The dosage may be administered as a single dose, in divided doses, or as continuous infusion.

The pharmaceutical composition may be administered on any convenient dosing schedule. Preferably, the pharmaceutical composition is administered once daily, twice daily, once every other day, once a week, or twice a week. More preferably, the pharmaceutical composition is administered once a week.

Preferably, the pharmaceutical composition is administered once a week in the dose of about 300 mg to about 1,500 mg. More preferably, the pharmaceutical composition is administered once a week in the dose of about 400 mg to about 1,000 mg. Even more preferably, the pharmaceutical composition is administered once a week in the dose of about 100 mg to about 200 mg.

The present invention also provides a method of inhibiting HIV infection comprising administering a pharmaceutical composition comprising, in admixture with a pharmaceutically acceptable excipient, a compound of formula (I), wherein $R_1$ is methoxy, m is 1, n is from 100 to 750, and p is 3.

Also contemplated within the scope of the invention is a method of inhibiting HIV infection comprising administering a pharmaceutical composition comprising, in admixture with a pharmaceutically acceptable excipient, a compound of formula (III), wherein n is from 10 to 1,000 and NHT1249 is a T1249 polypeptide covalently bonded through its terminal α-amino group. In one embodiment n is approximately 225, for example, 227. In another embodiment, n is approximately 450.

The following examples are provided to further illustrate the compounds, compositions, and methods of the present invention. These examples are illustrative only and are not intended to limit the scope of the invention in any way.

EXAMPLE 1

Preparation of mPEG$_{10K}$-butanoaldehyde mPEG of molecular weight 10,000 (30.0 g, 3 mmol) in 240 mL of toluene was azeotropically dried by refluxing for 2 hours, followed by the removal of 120 ml of toluene. The resulting solution was cooled to room temperature then potassium tert-butoxide (0.68 g, 6 mmol) in 20 ml of absolute tert-butanol and 20 ml of toluene was added to the PEG solution. The resulting mixture was stirred for two hours at room temperature under argon. Tert-butyl bromoacetate (1.00 mL, 6.75 mmol) was added to the reaction via syringe and the reaction was stirred overnight at room temperature under argon. The reaction solution was then condensed by rotary evaporation. The residue was precipitated by addition to diethyl ether. The precipitated mPEG$_{10k}$ t-butyl carboxymethyl ester product was filtered off and dried in vacuo. Yield: 28 g. NMR (d$_6$-DMSO): 1.40 ppm (t, 9H, —CH$_3$); 3.21 ppm (s, —OCH$_3$); 3.50 ppm (s, —O—CH$_2$CH$_2$—O—); 3.96 ppm (s, 2H, —O—CH$_2$—COO—).

mPEG$_{10k}$ t-butyl carboxymethyl ester (26.5 g) was then dissolved in 350 ml of 1N sodium hydroxide and the solution was stirred at room temperature overnight. The pH of the mixture was adjusted to 2.5 by addition of 6 N hydrochloric acid, and the mixture was extracted with dichloromethane. The organic layer was dried over sodium sulfate, filtered, concentrated, and precipitated into diethyl ether. The product m-PEG$_{10k}$-carboxymethyl acid was collected by filtration and dried under vacuum. Yield: 24 g. NMR (d$_6$-DMSO): 3.21 ppm (s, —OCH$_3$); 3.5 ppm (s, —O—CH$_2$CH$_2$—O—); 3.99 ppm (s, 2H, —O—CH$_2$—COOH).

mPEG$_{10k}$-carboxymethyl acid (6 g, 0.6 mmol) was then dissolved in anhydrous dichloromethane (30 mL) followed by the addition of 4-aminobutylraldehyde diethylacetal (140 ml, 0.9 mmol), 1-hydroxybenzotriazole (80 mg, 0.6 mmol), and dicyclohexylcarbodiimide (160 mg, 0.78 mmol). The mixture was stirred overnight at room temperature under argon. The reaction mixture was filtered, concentrated, and precipitated with mixture of 2-propanol and diethyl ether (1:1). The product mPEG$_{10k}$-butanoacetal was dried in vacuo overnight. Yield: 5.4 g. NMR (d$_6$-DMSO): 1.07–1.12 ppm (t, 6H, (—O—CH$_2$—CH$_3$)$_2$); 1.46 ppm (m, 4H, —NHCH$_2$CH$_2$CH$_2$—CH—); 3.08–3.11 ppm (q, 2H, —NHCH$_2$CH$_2$CH$_2$—CH—); 3.21 ppm (s, —OCH$_3$); 3.5 ppm (s, —O—CH$_2$CH$_2$—O—); 3.85 ppm (s, 2H, —O—CH$_2$—CO—NH—); 4.44 ppm (t, 1H, —NHCH$_2$CH$_2$CH$_2$—CH—); 7.67 ppm (—NH—).

mPEG$_{10k}$-butanoacetal (2 g, 0.2 mmol) was then dissolved in 20 ml of 80% CF$_3$COOH and the solution was stirred at room temperature overnight. The pH of the mixture was adjusted to 6.0 by addition of 1 N NaOH solution, and sodium chloride (10 wt %) was added and then the pH of the solution was adjusted to 7.0 by addition of 1 N NaOH. The mixture was extracted with dichloromethane. The organic layer was dried over sodium sulfate, filtered, concentrated, and precipitated into diethyl ether. The product mPEG$_{10k}$-butanoaldehyde was collected by filtration and dried under vacuum. Yield: 1.7 g. NMR (d$_6$-DMSO): 3.21 ppm (s, —OCH$_3$); 3.5 ppm (s, —O—CH$_2$CH$_2$—O—); 3.85 ppm (s, 2H, —O—CH$_2$—CO—NH—); 7.67 ppm (—NH—); 9.66 ppm (—CHO—).

EXAMPLE 2

Pegylation of T1249 with mPEG$_{10K}$-butanoaldehyde

Butanoaldehyde of PEG 10 kDa (mPEG$_{10k}$-CMAB) prepared according to Example 1 was added to 20 mg of T1249 (purity 93.7%) in 1.0 ml of buffer (50 mM potassium phosphate pH 6.5) in a molar ratio of 5 moles of reagent per one mole of T1249. The T1249 polypeptide was deacylated at the α-amino terminus, but protected at the carboxyl terminus by —NH$_2$. To the reaction mixture 10% (v/v) of 0.5 M sodium cyanoborohydride solution in water was added and stirred for 4 hours at room temperature. Pegylated T-1249 was purified from the reaction mixture using ion exchange chromatography (QA). A step gradient with increasing salt concentrations from 65 mM to 1 M NaCl in 20 mM Tris, pH 7.5 was used to separate pegylated T1249 and unmodified T1249.

EXAMPLE 3

Preparation of mPEG$_{20K}$-butanoaldehyde mPEG of molecular weight 20,000 (60.0 g, 3 mmol) in 800 ml of toluene was azeotropically dried by refluxing for 2 hours, followed by the removal of 200 ml of toluene. The resulting solution was cooled to room temperature then potassium tert-butoxide (0.68 g, 6 mmol) in 20 ml of absolute tert-butanol and 20 ml of toluene was added to the PEG solution. The resulting mixture was stirred for two hours at room temperature under argon. Tert-butyl bromoacetate (1.00 mL, 6.75 mmol) was added to the reaction via syringe and the reaction was stirred overnight at room temperature under argon. The reaction solution was then condensed by rotary evaporation. The residue, was precipitated by addition to diethyl ether. The precipitated product mPEG$_{20k}$ t-butyl carboxymethyl ester was filtered off and dried in vacuo. Yield: 56 g. NMR (d$_6$-DMSO): 1.42 ppm (t, 9H, —CH$_3$); 3.21 ppm (s, —OCH$_3$); 3.50 ppm (s, —O—CH$_2$CH$_2$—O—); 3.98 ppm (s, 2H, —O—CH$_2$—COO—).

mPEG$_{20k}$ t-butyl carboxymethyl ester (28 g) was then dissolved in 750 ml of 1N sodium hydroxide and the solution was stirred at room temperature overnight. The pH of the mixture was adjusted to 2.5 by addition of 6 N hydrochloric acid, and the mixture was extracted with dichloromethane. The organic layer was dried over sodium sulfate, filtered, concentrated, and precipitated into diethyl ether. The product m-PEG$_{20k}$-carboxymethyl acid was collected by filtration and dried under vacuum. Yield: 25 g. NMR (d$_6$-DMSO): 3.21 ppm (s, —OCH$_3$); 3.5 ppm (s, —O—CH$_2$CH$_2$—O—); 4.01 ppm (s, 2H, —O—CH$_2$—COOH).

mPEG$_{20k}$-carboxymethyl acid (20 g, 1.0 mmol) was then dissolved in anhydrous dichloromethane (100 mL) followed by the addition of 4-aminobutylraldehyde diethylacetal (0.77 ml, 4 mmol), 1-hydroxybenzotriazole (270 mg, 2.0 mmol), and dicyclohexylcarbodiimide (620 mg, 3.0 mmol). The mixture was stirred overnight at room temperature under argon. The reaction mixture was filtered, concentrated, and precipitated with mixture of 2-propanol and diethyl ether (1:1). The product mPEG$_{20k}$-butanoacetal was dried in vacuo overnight. Yield: 18.6 g. NMR (d$_6$-DMSO): 1.07–1.12 ppm (t, 6H, (—O—CH$_2$—CH$_3$)$_2$); 1.46 ppm (m, 4H, —NHCH$_2$CH$_2$CH$_2$—CH—); 3.08–3.11 ppm (q, 2H, —NHCH$_2$CH$_2$CH$_2$—CH—); 3.21 ppm (s, —OCH$_3$); 3.5 ppm (s, —O—CH$_2$CH$_2$—O—); 3.85 ppm (s, 2H, —O—CH$_2$—CO—NH—); 4.44 ppm (t, 1H, —NHCH$_2$CH$_2$CH$_2$—CH—); 7.67 ppm (—NH—).

mPEG$_{20k}$-butanoacetal (14.7 g, 0.73 mmol) was then dissolved in 200 ml of 10% CF$_3$COOH and the solution was stirred at room temperature overnight. The pH of the mixture was adjusted to 6.0 by addition of 1 N NaOH solution, and sodium chloride (10 wt %) was added and then the pH of the solution was adjusted to 7.0 by addition of 1 N NaOH. The mixture was extracted with dichloromethane. The organic layer was dried over sodium sulfate, filtered, concentrated, and precipitated into diethyl ether. The product mPEG$_{20k}$-butanoaldehyde was collected by filtration and dried under vacuum. Yield: 13.1 g. NMR (d$_6$-DMSO): 3.21 ppm (s, —OCH$_3$); 3.5 ppm (s, —O—CH$_2$CH$_2$—O—); 3.85 ppm (s, 2H, —O—CH$_2$—CO—NH—); 7.67 ppm (—NH—); 9.65.ppm (—CHO—).

EXAMPLE 4

Pegylation of T1249 with mPEG$_{20K}$-butanoaldehyde

Butanoaldehyde of PEG 20 kDa prepared according to Example 3 was added to 20 mg of T1249 (purity 93.7%) which was dissolved in 0.4 ml of 50 mM borate, pH 9.5 buffer and then diluted 10-fold with 100 mM potassium phosphate pH 6.5 in a molar ratio of 10 moles of reagent per one mole of T1249. The T1249 polypeptide was deacylated at the α-amino terminus, but protected at the carboxyl terminus by —NH2. To the reaction mixture 0.4 mL (10%, v/v) of 0.5 M sodium cyanoboro-hydride (NaBH$_3$CN) solution in water was added and stirred for 4 hrs at room temperature. The reaction mixture was then diluted 10-fold with equilibration buffer (20 mM Tris, pH 7.5) and filtered through a 0.45 μm filter. Pegylated T1249 was purified from the reaction mixture using anion, exchange chromatography (Q-Sepharose). A step gradient with increasing salt concentrations from 75 mM, 200 mM to 1 M NaCl in the equilibration buffer was used to separate di-pegylated, mono-pegylated and unmodified T1249 from, each other, respectively. The above experiment was repeated starting with 70 mg T1249, 1:10 molar excess of PEG$_{20K}$-butanoaldehyde and purified as described earlier. The mono-pegylated T1249 (200 mM NaCl eluate) pools from both experiments were combined, concentrated to approximately 2 mg/mL and diafiltered into the storage buffer (PBS buffer, pH 7.3) and stored at −20° C. until further use. An aliquot of the material was used to assay for antiviral activity.

EXAMPLE 5

% Mono-, % Di-, and % Tri-Pegylated T1249 with mPEG$_{20K}$-butanoaldehyde

The % Mono-, % di-, and % tri-pegylated T1249 with mPEG$_{20K}$-butanoaldehyde was determined through a series of experimnets where the T1249:PEG molar ratio, pH of the reaction solution, and reaction time were varied as seen below in Tables 1, 2, and 3. The purpose of these experiments was to optimize the pegylation parameters.

For example, in Table 1, butanoaldehyde of PEG 20 kDa (mPEG$_{20K}$-CMAB) prepared according to Example 3 was added to 5 mg of T1249 (purity 93.7%) in 50 mM potassium phosphate pH 6.5. The T1249 polypeptide was deacylated at the α-amino terminus, but protected at the carboxyl terminus by —NH$_2$. The molar ratio of PEG reagent to T1249 was 1:1, 1:2, and 1:5. To the reaction mixture 10% (v/v) of 0.5 M sodium cyanoborohydride solution in water was added. An aliquot was removed at the predetermined time interval of 2, 4, 6, and 24 hours at room temperature.

TABLE 1

Potassium Phosphate Buffer pH 6.5

| T1249:PEG Molar Ratio | Time Point | % mono-pegylated | % di-pegylated | % tri-pegylated | % T1249 |
|---|---|---|---|---|---|
| 1:1 | 2 h | 14 | 0.1 | 0 | 84 |
| 1:1 | 4 h | 18 | 0.19 | 0 | 81 |
| 1:1 | 6 h | 21 | 0.21 | 0 | 78 |
| 1:1 | 24 h | 25 | 0.91 | 0 | 72 |
| 1:2 | 2 h | 29 | 0.69 | 0 | 68 |
| 1:2 | 4 h | 34 | 1.14 | 0 | 63 |
| 1:2 | 6 h | 37 | 1.55 | 0 | 59 |
| 1:2 | 24 h | 39 | 3.16 | 0 | 54 |
| 1:5 | 2 h | 53 | 5 | 0 | 39 |
| 1:5 | 4 h | 59 | 9 | 0 | 26 |
| 1:5 | 6 h | 61 | 12 | 0 | 20 |
| 1:5 | 24 h | 55 | 23 | 0 | 15 |

For Table 2, butanoaldehyde of PEG 20 kDa (mPEG$_{20K}$-CMAB) prepared according to Example 3 was added to 5 mg of T1249 (purity 93.7%) in 50 mM potassium phosphate pH 6.0 in a molar ratio of ten moles of PEG reagent per one mole of T1249. The T1249 polypeptide was deacylated at the α-amino terminus, but protected at the carboxyl terminus by —NH$_2$. To the reaction mixture 10% (v/v) of 0.5 M sodium cyanoborohydride solution in water was added. An aliquot was removed at the predetermined time interval of 2, 4, 6, and 24 hours at room temperature.

TABLE 2

Potassium Phosphate Buffer pH 6.0

| T1249:PEG Molar Ratio | Time Point | % mono-pegylated | % di-pegylated | % tri-pegylated | % T1249 |
|---|---|---|---|---|---|
| 1:10 | 2 h | 60 | 11 | 0 | 22 |
| 1:10 | 4 h | 61 | 23 | 0 | 10 |
| 1:10 | 6 h | 59 | 24 | 5 | 7 |
| 1:10 | 24 h | 38 | 38 | 18 | 4 |

For Table 3, butanoaldehyde of PEG 20 kDa (mPEG$_{20K}$-CMAB) prepared according to Example 3 was added to 5 mg of T1249 (purity 93.7%) in 50 mM potassium phosphate pH 5.5 in a molar ratio of ten moles of PEG reagent per one mole of T1249. The T1249 polypeptide was deacylated at the α-amino terminus, but protected at the carboxyl terminus by —NH$_2$. To the reaction mixture 10% (v/v) of 0.5 M, sodium cyanoborohydride solution in water was added. An aliquot was removed at the predetermined time interval of 2, 4, 6, and 24 hours at room temperature.

TABLE 3

Potassium Phosphate Buffer pH 5.5

| T1249:PEG Molar Ratio | Time Point | % mono-pegylated | % di-pegylated | % tri-pegylated | % T1249 |
|---|---|---|---|---|---|
| 1:10 | 2 h | 47 | 7 | 0 | 41 |
| 1:10 | 4 h | 58 | 16 | 0 | 20 |
| 1:10 | 6 h | 60 | 22 | 3 | 10 |
| 1:10 | 24 h | 32 | 38 | 25 | 3 |

The percentage of mono-, di-, and tri-pegylated T1249, and unreacted free T1249 were obtained by reverse phase HPLC for every reaction mixture. The data exemplified in Tables 1, 2, and 3 above illustrates when optimal amounts of mono-pegylated T1249 is achieved under varying conditions of T1249:PEG molar ratio, pH, and reaction time. For example, in Table 1 an optimal mono-pegylation of 61% is shown at a T1249:PEG Molar Ratio of 1:5 and a time point of 6 h. In Table 2, an optimal mono-pegylation of 61% is shown at a T1249:PEG Molar Ratio of 1:10 and a time point of 4 h. In Table 3, an optimal mono-pegylation of 60% is shown at a T1249:PEG Molar Ratio of 1:10 and a time point of 6 h.

EXAMPLE 6

Determination of Pegylation Sites

To evaluate the site of PEG attachment to T1249, a series of experiments was performed. The results demonstrate that >95% of the modification is located at the N-terminal tryptophane residue. Additional modification sites may occur to a minor degree (<5%), but their exact identity is not clearly established.

In order to determine the PEG modification site, a sample was digested with endoproteinase Lys-C and the peptides separated by reverse phase HPLC. Individual peptide peaks were further analyzed with nano spray ESI (electrospray ionization) mass spectrometry, MALDI TOF (matrix assisted laser desorption/ionization-time of flight) mass spectrometry and N-terminal (Edman) sequencing. These procedures are summarized below.

Samples of 20K mono-pegylated-butanoaldehyde-T1249 (20k mPEG-CMAB-T1249) prepared according to Example 4 and T1249 (free α-amino terminus; carboxyl terminus protected by —NH$_2$) were proteolytically digested with endoproteinase Lys-C for 2 hours at ambient temperature with a sample to enzyme ratio of 10/1 (w/w). The reaction was stopped by adding acetic acid to a final concentration of 2% (v/v).

The separation of proteolytic peptides was done by reverse phase HPLC with a HP1100 HPLC system equipped with a Phenomenex Luna reversed phase column (C-18, 3µ, 150×200 mm). The solvent system consisted of water, acetonitrile and trifluoroacetic acid (0.05%). The gradient was from 5% to 64% organic solvent in 50 minutes at a flow rate of 0.2 ml/min. Peptide containing peaks were collected for further analysis.

All collected samples were then analyzed with nano spray ESI mass spectrometry on a Finnigan LCQ ion trap instrument. Individual peptides were identified based on experimental molecular weights. The PEG peptide containing fraction was also analyzed with MALDI TOF mass spectrometry on a Bruker Reflex instrument. Matrices used were trans-3-indoleacrylic acid or alpha-4-hdroxycinamic acid.

The PEG containing peptide fraction was then subjected to automated N-terminal (Edman) sequencing on a Perkin Elmer (ABI) precise instrument.

Figure 1:
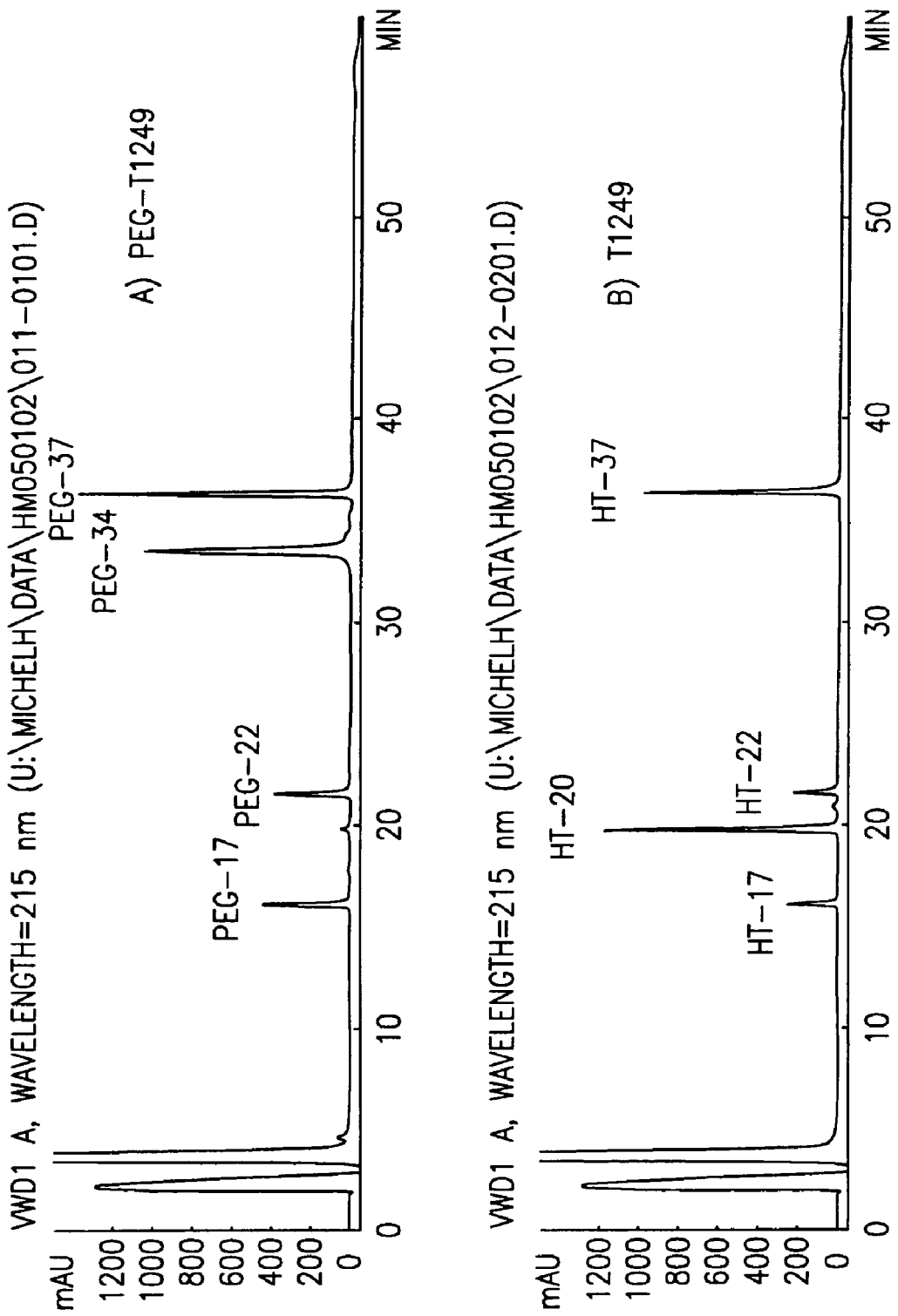
FIG. 1 shows a comparison of enzymatic digests of PEG-modified and unmodifed T1249. Digestion with endoproteinase Lys-C and subsequent separation with reversed phase HPLC is shown.

The results of the reverse phase HPLC analysis of the proteolytic fragments of pegylated T1249 are shown in FIG. 1. FIG. 1 shows the UV trace obtained from the reverse phase HPLC analysis of the two samples. The N-terminal peptide observed in the control T1249 (Peak HT-20 in FIG. 1B) is almost totally absent in the PEG modified T1249 (FIG. 1A). Instead one new peak appeared (Peak PEG-34 in FIG. 1A). It contains the PEG modified peptide(s).

Mass spectroscopic results obtained from the analysis of individual HPLC fractions are summarized in Table 4. All experimental molecular weights of non-modified peptides were compatible with the calculated ones.

TABLE 4

Analytical results obtained from collected HPLC fractions (see also FIG. 1).

| HPLC Peak[1] | MW (calc.)[2] Da | MW (exp.)[3] Da | N-terminal Sequence[4] | Peptide identity[5] | Seq ID |
|---|---|---|---|---|---|
| PEG-17 | 922.4 | 922.4 | n.A. | NEYELQK | Seq ID: 2 |
| PEG-22 | 1611.9 | 1611.7 | n.A. | ITALLEQAQIQQEK | Seq ID: 3 |
| PEG-34 | n.A. | 23082.6 | XQEWEQK | PEG-WQEWEQK | Seq ID: 4 |
| PEG-37 | 1122.5 | 1122.4 | n.A. | WASLWEWF-NH2 | Seq ID: 5 |
| HT-17 | 922.4 | 922.4 | n.A. | NEYELQK | Seq ID: 2 |
| HT-20 | 1032.5 | 1032.4 | n.A. | WQEWEQK | Seq ID: 4 |
| HT-22 | 1611.9 | 1611.7 | n.A. | ITALLEQAQIQQEK | Seq ID: 3 |
| HT-37 | 1122.5 | 1122.4 | n.A. | WASLWEWF-NH2 | Seq ID: 5 |

[1]see also FIG. 1;
[2]calculated exact mass in Da;
[3]measured mass in Da, nano spray ESI MS of non-modified peptides and MALDI TOF MS of PEG-modified peptides;
[4]automated Edman sequencing, n.A. = not available, x = none identified;
[5]based on MW compatability and/or Edman sequencing. The amino acid sequence of the unmodified T1249 sample is:
WQEWEQKITALLEQAQIQQEKNEYELQKLDKWASLWEWF-NH$_2$.

The MALDI TOF mass spectrum obtained from the intact PEG modified T1249 is shown in FIG. 2A. The measured molecular weight was 26758 Da. Note the presence of some non modified peptide. The origin of it is currently not known, however it could potentially be caused by the measurement in the mass spectrometer itself. The MALDI TOF mass spectrum obtained from fraction PEG-34 (FIG. 1) is shown in FIG. 2B. The measured molecular weight was 23083 Da. The molecular weight as well as the appearance of the mass spectrum identify this HPLC fraction PEG-34 as the one containing the PEG modified peptide(s). The presence of PEG in this HPLC fraction could also be shown by nano spray ESI mass spectrometry (data not shown).

Results from the automated N-terminal sequencing (Edman) are shown in FIG. 3. The observed major sequence was the N-terminal endo Lys-C peptide xQEWEQK. With exception of the first amino acid residue, all other amino acids were recovered in substantial yields. Essentially no tryptophane could be recovered in the first amino acid position (FIG. 3, cycle 3). The HPLC UV traces, the MALDI TOF mass spectrum as well as the results from the N-terminal sequencing identify the N-terminal tryptophane as the major PEG modification site.

The results above are consistent with the presence of a linkage between the polyethylene glycol aldehyde and the N-terminal tryptophane of T1249. Although a linkage directly to the tryptophane side chain cannot be entirely excluded, the results from the N-terminal sequencing appears to contradict the presence of a "blocking" PEG moiety at the N-terminal amino group.

EXAMPLE 7

Pegylation of T1249 with mPEG$_{10k}$-propionaldehyde

A propionaldehyde of PEG 10 kDa, having the following structure is used.

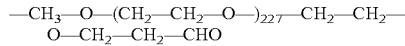

200 mg of mPEG10k-propionaldehyde was added to 20 mg of T1249 (purity 93.7%) in 1.0 ml of buffer (50 mM potassium phosphate pH 6.5) in a molar ratio of 5 moles of reagent per one mole of T1249. The T1249 polypeptide was deacylated at the α-amino terminus, but protected at the carboxyl terminus by —NH$_2$.

To the reaction mixture 10% (v/v) of 0.5 M sodium cyanoborohydride solution in water was added and stirred for 4 hours at room temperature. Pegylated T1249 was purified from the reaction mixture using ion exchange chromatography (QA). The structure of the pegylated T1249 follows:

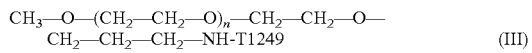

A linear gradient with increasing salt concentrations from 65 mM to 1 M NaCl in 20 mM Tris, pH 7.5 was used to separate pegylated T1249 and unmodified T1249. The percentage of mono-pegylated T1249 and unreacted free T1249 was then obtained by reverse phase HPLC and determined to be 31.7%.

EXAMPLE 8 cMAGI/MAGI Antiviral Assays

These assays score for reduction of infectious virus titer employing the indicator cell lines MAGI (Multinuclear Activation of a Galactosidase Indicator) or the CCR5-expressing derivative cMAGI. The MAGI cell line was derived from parental HeLa cells by introducing genes for CD4 and an HIV-1 LTR-driven b-gal reporter with an amphotropic retrovirus vector (Kimpton J, Emerman M, J Virol 66:2232-9, 1992). The cMAGI cell line was derived from the MAGI cell line by introduction of the CCR5 gene using the amphotropic retroviral vector, PA317 (Chackerian B, Long E M, Luciw P A, Overbaugh J, J Virol 71:3932-9, 1997). The cMAGI cells support replication of primary NSI (R5) isolates and laboratory adapted X4 viruses, while the MAGI cells support replication of only X4 viruses. Both cell lines exploit the ability of HIV-1 tat to transactivate the expression of a b-galactosidase reporter gene driven by the HIV-LTR. The b-gal reporter has been modified to localize in the nucleus and can be detected with the X-gal substrate as intense nuclear staining within a few days of infection. The number of stained nuclei can thus be interpreted as equal to the number of infectious virions in the challenge inoculum if there is only one round of infection prior to staining.

An inhibitor of infection and cell-cell fusion, e.g., T1249 (Wild C, Greenwell T, Matthews T, AIDS Res Hum Retroviruses 9:1051-3, 1993), was added 24 hrs post-infection in order to permit a readout that confidently represents a single round of infection. Infected cells were enumerated using a CCD-imager and both primary and laboratory adapted isolates showed a linear relationship between virus input and the number of infected cells visualized by the imager. In the MAGI and cMAGI assays a 50% reduction in infectious titer ($V_n/N_o=0.5$) is significant and provides the primary cutoff value for assessing antiviral activity. A 90% reduction in infectious titer ($V_n/N_o$) is used as an additional cutoff value on assessing antiviral activity.

Each test compound dilution was tested in duplicate against a virus inoculum adjusted to yield approximately 1500–2000 infected cells/well of a 48 well micro titer plate. The test compound was added to the cMAGI or MAGI cells, followed by the virus inocula, and 24 hrs later, an inhibitor of infection and cell-cell fusion (Wild C, Greenwell T, Matthews T, AIDS Res Hum Retroviruses 9:1051-3, 1993) was added to prevent secondary rounds of infection and cell-cell virus spread. The cells were cultured for 2 more days, fixed and stained with the X-gal substrate to detect infected cells. The number of infected cells for each control and test compound dilution were determined with the CCD-imager. IC50 is defined as the dilution of a test compound resulting in a 50% reduction in infectious virus titer. IC90 is defined as the dilution resulting in a 90% reduction in infectious titer.

EXAMPLE 9

IC50/IC90 for Pegylated T1249

IC50 and IC90 results for T1249 and T1249 pegylated with mPEG$_{20K}$-butanoaldehyde (Example 4), hereinafter "mPEG$_{20k}$-CMAB-T1249," is shown in Table 5 below. The IC$_{50}$ and IC$_{90}$ values were determined in accordance with Example 8.

TABLE 5

| | IC50 and IC90 results. | |
|---|---|---|
| Peptide | IC50 (μg/ml) | IC90 (μg/ml) |
| T1249 | 0.003 | 0.023 |
| mPEG$_{20k}$-CMAB-T1249 | 0.041 (batch 1) | 0.206 (batch 1) |
| | 0.170 (batch 2) | 0.835 (batch 2) |

Reduction (IC50, 13.7-fold and IC90, 9-fold for batch 1) of in vitro anti-viral activity was observed with mPEG$_{20k}$-CMAB-T1249 compared to the parent T1249 molecule. However, this loss in in vitro activity is not predictive of the in vivo biological activity as demonstrated by the results illustrated in Example 12 (See, FIG. 6).

EXAMPLE 10

Pharmacokinetics of T1249 Pegylated with mPEG$_{20k}$-propionaldehyde

Study Design 9 male Wistar rats (Charles River Laboratories, Wilmington, Del.) (n=3/time point) received a single subcutaneous dose of T1249 pegylated with mPEG$_{20k}$-propionaldehyde (Example 4).

The mPEG$_{20k}$-CMAB-T1249 was suspended in water and titrated with NaOH to bring to a pH of 6.8. The mPEG$_{20k}$-CMAB-T1249 suspension was then solubilized in a minimum volume of sodium carbonate buffer and diluted with PBS buffer to a pH of 7.3–7.4. The amount of PEG-T1249 employed was sufficient to provide a concentration of 150 mg mPEG$_{20k}$-CMAB-T1249 per ml in the final formulation. The rats were dosed at 8 mg of active ingredient/kg body weight.

After dose administration, about 1 ml of blood was collected from the retro-orbital sinus at each time point. The time points were 0.5, 1, 3, 6, 8, 16, 24, 32, 48, 72, and 96 hours after dose administration. All blood samples were kept at room temperature for up to 30 minutes and serum was separated with cold centrifugation.

Bioanalytical Method

All blood samples were separated on a reverse phase HPLC C18 column using a linear gradient consisting of 0.05 M ammonium acetate and acetonitrile. Absorbance was monitored at 280 nm. Concentrations were extrapolated from a plot (area under the curve v. [mPEG$_{20k}$-CMAB-T1249]) using mPEG$_{20k}$-CMAB-T1249 spiked serum extracts as calibration standards.

The reported pharmacokinetic parameters were derived from pooled serum concentration profiles of mPEG$_{20k}$-CMAB-T1249, its metabolite, and the combination of the two, using non-compartmental analysis via WinNonlin, version 3.3 (Pharsight Corporation, Mountain View, Calif.), a commercial kinetic analysis software package.

Results

Figure 4:
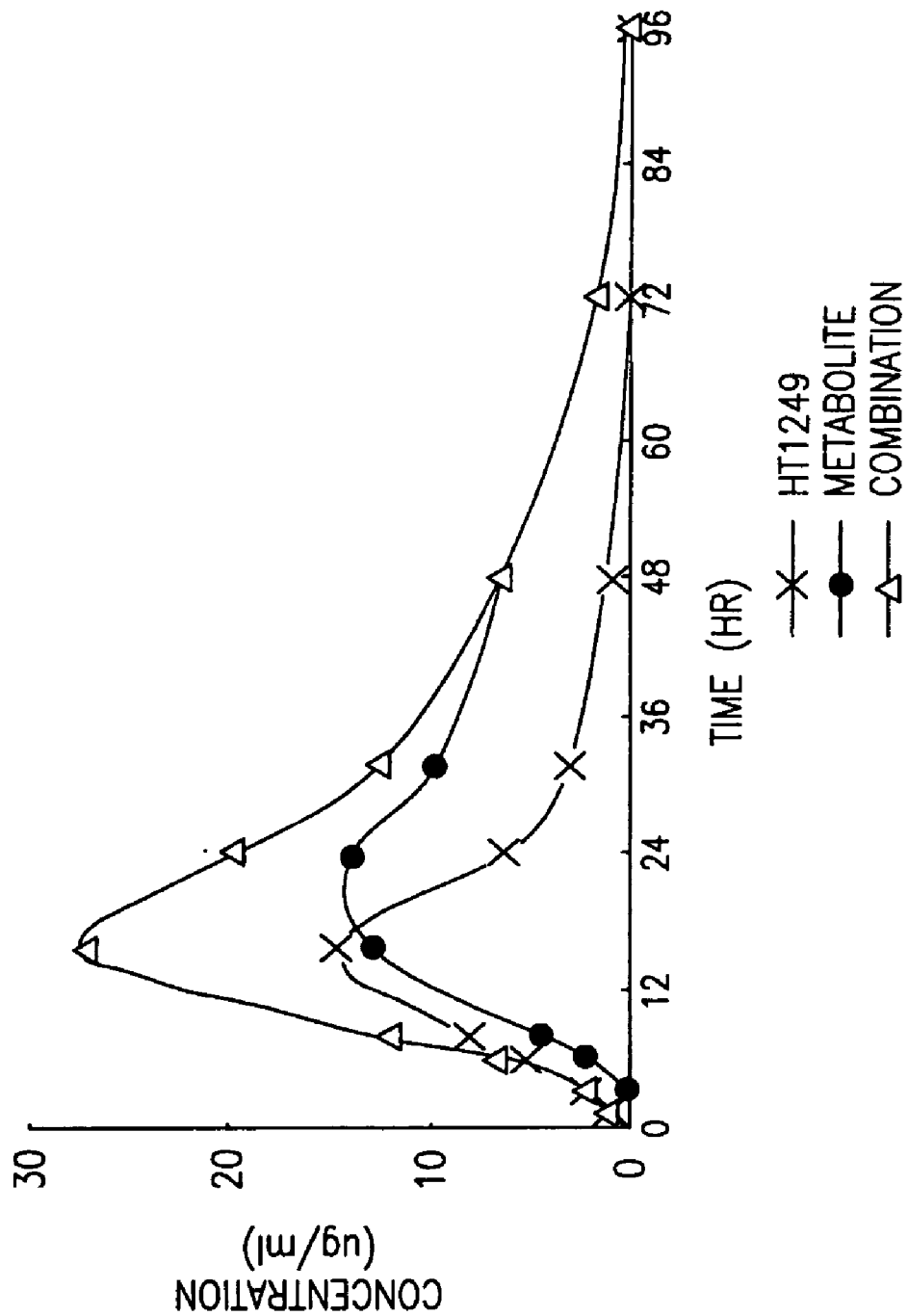
FIG. 4 shows the concentration-time profile of $mPEG_{20k}$-CMAB-T1249 in rats after a single subcutaneous dose administration.

FIG. 4 shows the concentration-time profile of mPEG$_{20k}$-CMAB-T1249 in rats after a single subcutaneous dose administration. At the 0.5 hour time point no level of mPEG$_{20k}$-CMAB-T1249 or a metabolite was detected, indicating a slow absorption process from the injection site. For the metabolite, the first detectable concentration was found at 6 hours post dosing, which represents a slow course of metabolite formation. The lowest serum concentrations of mPEG$_{20k}$-CMAB-T1249 and its metabolite were detected at 48 and 72 hours post dosing, respectively.

Systemic Cl/F and V$_d$/F, AUC (0–48 hours or 0–72 hours), C$_{max}$, T$_{max}$, and half-life are reported in Table 6, below.

TABLE 6

Pharmacokinetic parameters for mPEG$_{20k}$-CMAB-T1249 in rats.

| Parameter (unit) | mPEG$_{20k}$-CMAB-T1249 | mPEG$_{20k}$-CMAB-T1249 Metabolite | Parent and Metabolite |
|---|---|---|---|
| AUC (μg hr/ml) | 279[a] | 508[b] | 766[b] |
| C$_{max}$ (μg/ml) | 14.8 | 13.9 | 27.2 |
| T$_{1/2terminal}$ (hr) | 8.9 | 15.7 | 13.8 |
| Cl/F (ml/hr/kg) | 27.4 | 14.6 | 10.0 |
| V$_d$/F (ml/kg) | 353 | 330 | 199 |
| T$_{max}$ (hr) | 16 | 24 | 16 |

[a] AUC$_{0-48hr}$;
[b] AUC$_{0-72hr}$

EXAMPLE 11

Pharmacokinetics of T1249

Study Design

Each treatment group, consisted of 9 Sprague-Dawley rats (Charles River Laboratories, Wilmington, Del.) per sex. Each member of the group received a single subcutaneous or intravenous dose of T1249 (batch 2 referenced in Example 9/Table 5). The rats were dosed at either 1.2 or 15 mg of the active ingredient/kg of body weight.

Blood samples were collected from test animals over a twelve hour time period from three rats per sex per group at each time point. The time points were 0.5, 1, 2, 4, 6, 8, 10, and 12 hours after dose administration.

Bioanalytical Method

The blood samples were analyzed using a T1249 PcAb ECLIA assay. T1249 PcAb ECLIA is a noncompetitive, two site immunoassay that utilizes two different preparations of rabbit PcAb specific for T1249. In this assay, T1249 determinations are preformed by first incubating the diluted test sample in a tube that also contains biotin-labeled antibody (preparation A) and ruthenium-labeled antibody (preparation B). In the next step, streptavidin-coated magnetic beads are added to the tube in order to capture the antibody-peptide-antibody immune complexes (sandwiches) that have formed. The mixture is then pumped through a flow-cell in the analyzer, after which an electrical current is applied to a magnet adjacent to the flow-cell. Light is generated through cyclical oxidation-reduction reactions between the ruthenium metal ions that are conjugated to the detector antibodies and tripropylamine ions that are present in excess in the assay buffer. This light energy is the measured end-point. A sample containing appreciable amount of T1249 presents a higher signal compared to a sample containing little or no T1249.

Results

Figure 5:
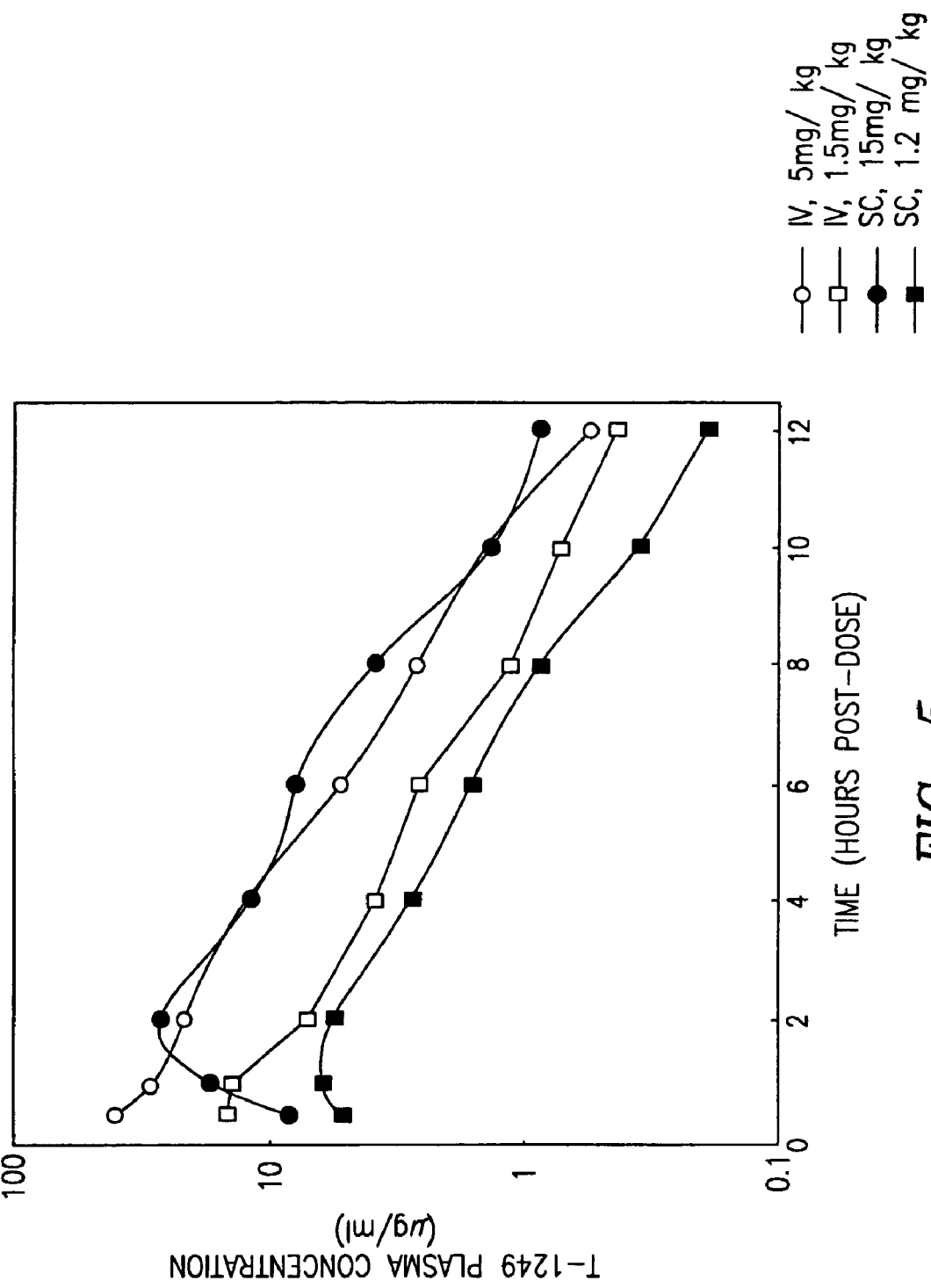
FIG. 5 shows the concentration-time profile of T1249 in rats after a single subcutaneous dose administration.

FIG. 5 shows the concentration-time profile of T1249 in rats after a single subcutaneous or intravenous dose administration.

T$_{max}$, half-life, AUC (0–12 hours and 0-∞ hours), and C$_{max}$ are reported in Table 7, below.

TABLE 7

Pharmacokinetic parameters for T1249 in rats.

| | Dose Groups | | | |
|---|---|---|---|---|
| Parameter (unit) | 1.2 mg/kg (SC) | 15 mg/kg (SC) | 1.5 mg/kg (IV) | 5.0 mg/kg (IV) |
| T$_{1/2terminal}$ (hr) | 2.02 | 2.00 | 2.46 | 1.86 |
| T$_{max}$ (hr) | 1.09 | 1.88 | — | — |
| C$_{max}$ (μg/ml) | 6.37 | 21.5 | 15.7 | 46.3 |
| AUC$_{(0-12hr)}$ (μg hr/ml) | 27.0 | 107 | 45.6 | 118 |
| AUC$_{(0-\infty)}$ (μg hr/ml) | 27.6 | 110 | 47.1 | 120 |

Considering the pharmacokinetic data for mPEG$_{20k}$-CMAB-T1249 (Table 6) and the 15 mg/kg subcutaneous dosing with T1249 (Table 7), mPEG$_{20k}$-CMAB-T1249 exhibits a 4.5-fold increase in terminal half-life. The higher T$_{max}$ reflects a slower clearance for mPEG$_{20k}$-CMAB-T1249 compared to T1249 while having a similar C$_{max}$. In addition, once the data from Table 7 is normalized for the difference in dose (15 mg/kg normalized to 8 mg/kg as in Example 10), a five-fold increase over T1249 in AUC was observed for mPEG$_{20k}$-CMAB-T1249 (57.1 μg hr/ml (normalized) for T1249 versus 279 μg hr/ml for mPEG$_{20k}$-CMAB-T1249).

EXAMPLE 12

Effect of T1249 and mPEG$_{20k}$-CMAB-T1249 on HIV-1 Viral Load in Mice

HuPBMC-SCID mice per treatment group (except PEG control which had 6 mice) were employed. On Day 0, each treatment group received a p.m. treatment after infection with HIV isolate. Thereafter, each treatment group received 2 treatments a day (a.m. and p.m.) from day 1 to day 6. The mice were harvested on day 7. See Table 8 for dosing details. Plasma samples for T1249 analysis were collected about 14 hours after last dose administration.

TABLE 8

| Dosing scheme. | | | | |
|---|---|---|---|---|
| Dose Group | Dose | Mice/group | Day | Activity |
| Saline Control | 0 mg/day | 9 | 1–6 | am dose pm dose |
| T1249 | 0.7 mg/day | 9 | 1–6 | am dose |
|  | 2 mg/day | 9 |  | pm dose |
|  | 7 mg/day | 9 |  |  |
| mPEG$_{20k}$-CMAB-T1249 | 0.7 mg/day | 9 | 1–6 | am dose |
|  | 2 mg/day | 9 |  | pm dose |
|  | 7 mg/day | 9 |  |  |
| PEG Control | 7 mg/day | 6 | 1–6 | am dose pm dose |
| All |  |  | 7 | harvest |

HIV-1 in plasma was determined by real-time quantitative PCR. Plasma was harvested for T1249 compound quantification. Frozen plasma samples then underwent compound analysis.

FIG. 6 shows the effect of T1249 and mPEG$_{20k}$-CMAB-T1249 dosing on the HIV-1 viral load in SCID mice.

T1249 and mPEG$_{20k}$-CMAB-T1249 are equally active in vivo. The results show no discernable difference in in vivo viral suppression activity as measured against plasma concentration of the tested compound.

The above results indicate the advantageous properties of the invention, the equivalent in vivo biological activity of mPEG$_{20k}$-CMAB-T1249 and T1249 at equal plasma concentrations (Example 12), and far superior pharmacokinetic profile of mPEG$_{20k}$-CMAB-T1249 as demonstrated by the comparison of Examples 10 and 11.

The invention being thus described, it will be obvious that the same may be varied in many ways. Such variations are not to be regarded as a departure from the spirit and scope of the invention and all such modifications are intended to be included within the scope of the following claims.

What is claimed is:

1. A compound of formula (I),

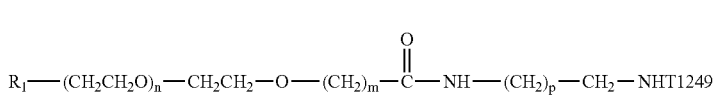

wherein $R_1$ is a capping group, m is from 1 to 17, n is from 10 to 1,000, p is from 1 to 3, and NHT1249 is a T1249 polypeptide covalently bonded through its terminal α-amino group.

2. A compound according to claim 1, wherein $R_1$ is selected from the group consisting of halogen, epoxide, maleimide, orthopyridyl disulfide, tosylate, isocyanate, hydrazine hydrate, cyanuric halide, N-succinimidyloxy, sulfo-N-succinimidyloxy, 1-benzotriazolyloxy, 1-imidazolyloxy, p-nitrophenyloxy, and

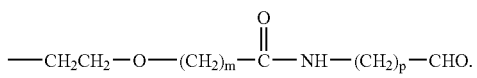

3. A compound according to claim 1, wherein $R_1$ is

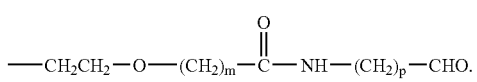

4. A compound according to claim 1, wherein $R_1$ is selected from the group consisting of hydrogen, hydroxy, lower alkyl, lower alkoxy, lower cycloalkyl, lower alkenyl, aryl, and heteroaryl.

5. A compound according to claim 1, wherein $R_1$ is selected from the group consisting of methoxy, hydroxy, and benzyloxy.

6. A compound according to claim 5, wherein $R_1$ is methoxy.

7. A compound according to claim 1, wherein p is 3.

8. A compound according to claim 7, wherein $R_1$ is selected from the group consisting of methoxy, hydroxy, or benzyloxy.

9. A compound according to claim 7, wherein m is from 1 to 14.

10. A compound according to claim 9, wherein m is from 1 to 7.

11. A compound according to claim 10, wherein m is from 1 to 4.

12. A compound according to claim 7, wherein n is from 20 to 1,000.

13. A compound according to claim 12, wherein n is from 50 to 1,000.

14. A compound according to claim 13, wherein n is from 75 to 1,000.

15. A compound according to claim 1, wherein p is 3, $R_1$ is methoxy, m is 1, and n is from 100 to 750.

16. A compound according to claim 1, wherein p is 2.

17. A compound according to claim 16, wherein $R_1$ is selected from the group consisting of methoxy, hydroxy, or benzyloxy.

18. A compound according to claim 16, wherein m is from 1 to 14.

19. A compound according to claim 18, wherein m is from 1 to 7.

20. A compound according to claim 19, wherein m is from 1 to 4.

21. A compound according to claim 16, wherein n is from 20 to 1,000.

22. A compound according to claim 21, wherein n is from 50 to 1,000.

23. A compound according to claim 22, wherein n is from 75 to 1,000.

24. A compound according to claim 1, wherein p is 2, $R_1$ is methoxy, m is 1, and n is from 100 to 750.

25. A compound according to claim 1, wherein p is 1.

26. A compound according to claim 25, wherein $R_1$ is selected from the group consisting of methoxy, hydroxy, or benzyloxy.

27. A compound according to claim 25, wherein m is from 1 to 14.

28. A compound according to claim 27, wherein m is from 1 to 7.

29. A compound according to claim 28, wherein m is from 1 to 4.

30. A compound according to claim 25, wherein n is from 20 to 1,000.

31. A compound according to claim 30, wherein n is from 50 to 1,000.

32. A compound according to claim 31, wherein n is from 75 to 1,000.

33. A compound according to claim 1, wherein p is 1, $R_1$ is methoxy, m is 1, and n is from 100 to 750.

34. A compound of formula:

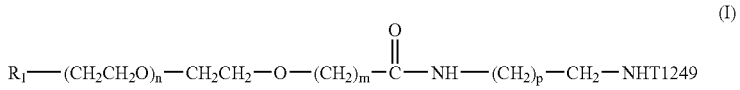
(III)

wherein n is from 10 to 1,000 and NHT1249 is a T1249 polypeptide covalently bonded through its terminal α-amino group.

35. A compound according to claim 34, wherein n is approximately 225.

36. A compound according to claim 34, wherein n is approximately 450.

37. A pharmaceutical composition comprising, in admixture with a pharmaceutically acceptable excipient, a compound of formula:

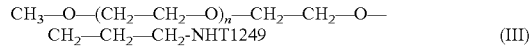
(I)

wherein
$R_1$ is a capping group,
m is from 1 to 17,
n is from 10 to 1,000,
p is from 1 to 3, and
NHT1249 is a T1249 polypeptide covalently bonded through its terminal α-amino group.

38. A pharmaceutical composition according to claim 37, wherein $R_1$ is selected from the group consisting of halogen, epoxide, maleimide, orthopyridyl disulfide, tosylate, isocyanate, hydrazine hydrate, cyanuric halide, N-succinimidyloxy, sulfo-N-succinimidyloxy, 1-benzotriazolyloxy, 1-imidazolyloxy, p-nitrophenyloxy, and

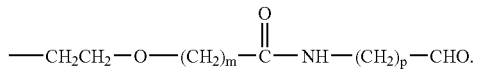

39. A pharmaceutical composition according to claim 37, wherein $R_1$ is

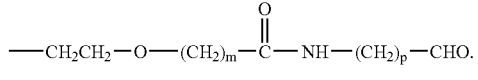

40. A pharmaceutical composition according to claim 37, wherein $R_1$ is selected from the group consisting of hydrogen, hydroxy, lower alkyl, lower alkoxy, lower cycloalkyl, lower alkenyl, aryl, and heteroaryl.

41. A pharmaceutical composition according to claim 37, wherein $R_1$ is selected from the group consisting of methoxy, hydroxy, and benzyloxy.

42. A pharmaceutical composition according to claim 37, wherein $R_1$ is methoxy.

43. A pharmaceutical composition according to claim 37, wherein p is 3.

44. A pharmaceutical composition according to claim 43, wherein $R_1$ is selected from the group consisting of methoxy, hydroxy, or benzyloxy.

45. A pharmaceutical composition according to claim 44, wherein m is from 1 to 14.

46. A pharmaceutical composition according to claim 45, wherein m is from 1 to 7.

47. A pharmaceutical composition according to claim 46, wherein m is from 1 to 4.

48. A pharmaceutical composition according to claim 44, wherein n is from 20 to 1,000.

49. A pharmaceutical composition according to claim 48, wherein n is from 50 to 1,000.

50. A pharmaceutical composition according to claim 49, wherein n is from 75 to 1,000.

51. A pharmaceutical composition according to claim 37, wherein p is 3, $R_1$ is methoxy, m is 1, and n is from 100 to 750.

52. A pharmaceutical composition according to claim 37, wherein p is 2.

53. A pharmaceutical composition according to claim 52, wherein $R_1$ is selected from the group consisting of methoxy, hydroxy, or benzyloxy.

54. A pharmaceutical composition according to claim 52, wherein m is from 1 to 14.

55. A pharmaceutical composition according to claim 54, wherein m is from 1 to 7.

56. A pharmaceutical composition according to claim 55, wherein m is from 1 to 4.

57. A pharmaceutical composition according to claim 52, wherein n is from 20 to 1,000.

58. A pharmaceutical composition according to claim 57, wherein n is from 50 to 1,000.

59. A pharmaceutical composition according to claim 58, wherein n is from 75 to 1,000.

60. A pharmaceutical composition according to claim 37, wherein p is 2, $R_1$ is methoxy, m is 1, and n is from 100 to 750.

61. A pharmaceutical composition according to claim 37, wherein p is 1.

62. A pharmaceutical composition according to claim 61, wherein $R_1$ is selected from the group consisting of methoxy, hydroxy, or benzyloxy.

63. A pharmaceutical composition according to claim 61, wherein m is from 1 to 14.

64. A pharmaceutical composition according to claim 63, wherein m is from 1 to 7.

65. A pharmaceutical composition according to claim 64, wherein m is from 1 to 4.

66. A pharmaceutical composition according to claim 61, wherein n is from 20 to 1,000.

67. A pharmaceutical composition according to claim 66, wherein n is from 50 to 1,000.

68. A pharmaceutical composition according to claim 67, wherein n is from 75 to 1,000.

69. A pharmaceutical composition according to claim 37, wherein p is 1, $R_1$ is methoxy, m is 1, and n is from 100 to 750.

70. A pharmaceutical composition according to claim 37 in the form of a lypholized powder.

71. A pharmaceutical composition according to claim 37 in the form of an injectable solution or suspension.

72. A pharmaceutical composition according to claim 51 in the form of a lypholized powder.

73. A pharmaceutical composition according to claim 52 in the form of an injectable solution or suspension.

74. A pharmaceutical composition according to claim 37, in unit dosage form.

75. A pharmaceutical composition according to claim 74, wherein the unit dosage form is an injectable solution or suspension.

76. A pharmaceutical composition according to claim 74, wherein the unit dosage form is a transdermal delivery device.

77. A pharmaceutical composition according to claim 51, in unit dosage form.

78. A pharmaceutical composition according to claim 77, wherein the unit dosage form is an injectable solution or suspension.

79. A pharmaceutical composition according to claim 77, wherein the unit dosage form is a transdermal delivery device.

80. A pharmaceutical composition comprising, in admixture with a pharmaceutically acceptable excipient, a compound of formula:

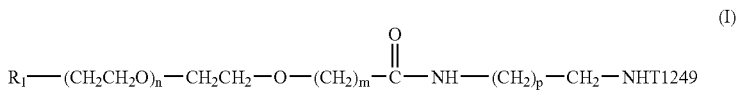

(III)

wherein n is from 10 to 1,000 and NHT1249 is a T1249 polypeptide covalently bonded through its terminal α-amino group.

81. A pharmaceutical composition according to claim 80, wherein n is approximately 225.

82. A pharmaceutical composition according to claim 80, wherein n is approximately 450.

83. A method of inhibiting HIV infection comprising administering a pharmaceutical composition comprising, in admixture with a pharmaceutically acceptable excipient, a compound of formula:

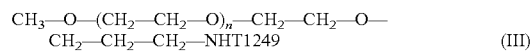

(I)

wherein
$R_1$ is a capping group,
m is from 1 to 17,
n is from 10 to 1,000,
p is from 1 to 3, and
NHT1249 is a T1249 polypeptide covalently bonded through its terminal α-amino group.

84. A method according to claim 83, wherein $R_1$ is selected from the group consisting of halogen, epoxide, maleimide, orthopyridyl disulfide, tosylate, isocyanate, hydrazine hydrate, cyanuric halide, N-succinimidyloxy, sulfo-N-succinimidyloxy, 1-benzotriazolyloxy, 1-imidazolyloxy, p-nitrophenyloxy, and

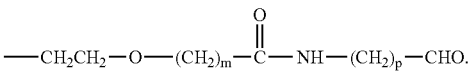

85. A method according to claim 83, wherein $R_1$ is

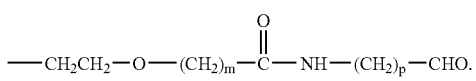

86. A method according to claim 83, wherein $R_1$ is selected from the group consisting of hydrogen, hydroxy, lower alkyl, lower alkoxy, lower cycloalkyl, lower alkenyl, aryl, and heteroaryl.

87. A method according to claim 83, wherein $R_1$ is selected from the group consisting of methoxy, hydroxy, and benzyloxy.

88. A method according to claim 83, wherein $R_1$ is methoxy.

89. A method according to claim 83, wherein p is 3.

90. A method according to claim 89, wherein $R_1$ is selected from the group consisting of methoxy, hydroxy, or benzyloxy.

91. A method according to claim 89, wherein m is from 1 to 14.

92. A method according to claim 91, wherein m is from 1 to 7.

93. A method according to claim 92, wherein m is from 1 to 4.

94. A method according to claim 89, wherein n is from 20 to 1,000.

95. A method according to claim 94, wherein n is from 50 to 1,000.

96. A method according to claim 95, wherein n is from 75 to 1,000.

97. A method according to claim 83, wherein p is 3, $R_1$ is methoxy, m is 1, and n is from 100 to 750.

98. A method according to claim 83, wherein p is 2.

99. A method according to claim 98, wherein $R_1$ is selected from the group consisting of methoxy, hydroxy, or benzyloxy.

100. A method according to claim 98, wherein m is from 1 to 14.

101. A method according to claim 100, wherein m is from 1 to 7.

102. A method according to claim 101, wherein m is from 1 to 4.

103. A method according to claim 98, wherein n is from 20 to 1,000.

104. A method according to claim 103, wherein n is from 50 to 1,000.

105. A method according to claim 104, wherein n is from 75 to 1,000.

106. A method according to claim 83, wherein p is 2, $R_1$ is methoxy, m is 1, and n is from 100 to 750.

107. A method according to claim 83, wherein p is 1.

108. A method according to claim 107, wherein $R_1$ is selected from the group consisting of methoxy, hydroxy, or benzyloxy.

109. A method according to claim 107, wherein m is from 1 to 14.

110. A method according to claim 109, wherein m is from 1 to 7.

111. A method according to claim 110, wherein m is from 1 to 4.

112. A method according to claim 107, wherein n is from 20 to 1,000.

113. A method according to claim 112, wherein n is from 50 to 1,000.

114. A method according to claim 113, wherein n is from 75 to 1,000.

115. A method according to claim 83, wherein p is 1, $R_1$ is methoxy, m is 1, and n is from 100 to 750.

116. A method according to claim 83, wherein the pharmaceutical composition is administered by injection.

117. A method according to claim 116, wherein the pharmaceutical composition is injected intraperitoneally, intramuscularly, subcutaneously, intravenously, or by continuous infusion.

118. A method according to claim 117, wherein the pharmaceutical composition is injected subcutaneously.

119. A method according to claim 83, wherein the pharmaceutical composition is administered once a day.

120. A method according to claim 83, wherein the pharmaceutical composition is administered twice a week.

121. A method according to claim 83, wherein the pharmaceutical composition is administered once a week.

122. A method according to claim 83, wherein the pharmaceutical composition is administered every other day.

123. A method according to claim 83, wherein the pharmaceutical composition is administered twice a day.

124. A method according to claim 83, wherein the pharmaceutical composition is administered in an amount of from about 50 mg to about 300 mg per administration.

125. A method according to claim 83, wherein the pharmaceutical composition is administered in an amount of from about 100 mg to about 200 mg per administration.

126. A method according to claim 97, wherein the pharmaceutical composition is administered by injection.

127. A method according to claim 126, wherein the pharmaceutical composition is injected intraperitoneally, intramuscularly, subcutaneously, intravenously, or by continuous infusion.

128. A method according to claim 127, wherein the pharmaceutical composition is injected subcutaneously.

129. A method according to claim 97, wherein the pharmaceutical composition is administered once a day.

130. A method according to claim 97, wherein the pharmaceutical composition is administered twice a week.

131. A method according to claim 97, wherein the pharmaceutical composition is administered once a week.

132. A method according to claim 97, wherein the pharmaceutical composition is administered every other day.

133. A method according to claim 97, wherein the pharmaceutical composition is administered twice a day.

134. A method according to claim 97, wherein the pharmaceutical composition is administered in an amount of from about 50 mg to about 300 mg per administration.

135. A method according to claim 134, wherein the pharmaceutical composition is administered in an amount of from about 100 mg to about 200 mg per administration.

136. A method of inhibiting HIV infection comprising administering a pharmaceutical composition comprising, in admixture with a pharmaceutically acceptable excipient, a compound of formula:

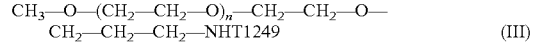

wherein n is from 10 to 1,000 and NHT1249 is a T1249 polypeptide covalently bonded through its terminal α-amino group.

137. A method according to claim 136, wherein n is approximately 225.

138. A method according to claim 136, wherein n is approximately 450.

139. A method according to claim 136, wherein the pharmaceutical composition is administered in an amount of from about 300 mg to about 1500 mg per week in a single dose.

140. A method according to claim 139, wherein the pharmaceutical composition is administered in an amount of from about 400 mg to about 1000 mg per week in a single dose.

141. A method according to claim 140, wherein the pharmaceutical composition is administered in an amount of from about 500 mg to about 800 mg per week in a single dose.

142. A compound of formula:

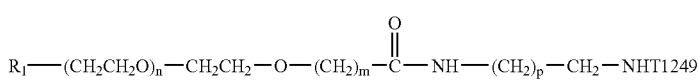

(I)

wherein
  $R_1$ is methoxy,
  m is 1,
  n is from 100 to 750,
  p is 3, and
  NHT1249 is a T1249 polypeptide covalently bonded through its terminal α-amino group.

143. A pharmaceutical composition comprising, in admixture with a pharmaceutically acceptable excipient, a compound of formula:

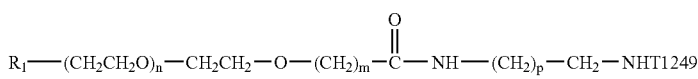

(I)

wherein
  $R_1$ is methoxy,
  m is 1,
  n is from 100 to 750,
  p is 3, and
  NHT1249 is a T1249 polypeptide covalently bonded through its terminal α-amino group.

144. A method of inhibiting HIV infection comprising administering a pharmaceutical composition comprising, in admixture with a pharmaceutically acceptable excipient, a compound of formula:

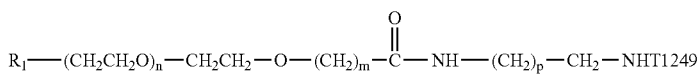

(I)

wherein
  $R_1$ is methoxy,
  m is 1,
  n is from 100 to 750,
  p is 3, and
  NHT1249 is a T1249 polypeptide covalently bonded through its terminal α-amino group.

145. A method for attaching a polyethylene glycol molecule to a T1249 polypeptide comprising reacting a T1249 polypeptide with a polyethylene glycol aldehyde of formula:

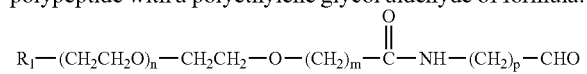

wherein
  $R_1$ is a capping group,
  m is from 1 to 17,
  n is from 10 to 1,000, and
  p is from 1 to 3;

to produce a compound of formula:

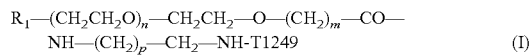

(I)

wherein the polyethylene glycol aldehyde molecule is bonded to the N-terminal amino group of the T1249 polypeptide.

146. A method according to claim 145 wherein the T1249 polypeptide is reacted with the polyethylene glycol molecule at a pH sufficiently acidic to selectively activate the α-amino group at the amino terminus of the polypeptide.

147. A method according to claim 145 wherein the pH is from about 5.5 to about 7.4.

148. A method according to claim 147 wherein the pH is about 6.5.

149. A method according to claim 145 further comprising isolating the pegylated T1249 polypeptide.

* * * * *

SEQUENCE LISTING

```
<160> NUMBER OF SEQ ID NOS: 5

<210> SEQ ID NO 1
<211> LENGTH: 39
<212> TYPE: PRT
<213> ORGANISM: Artificial
<220> FEATURE:
<223> OTHER INFORMATION: Peptide sequence was synthetically derived.
<220> FEATURE:
<221> NAME/KEY: MOD_RES
<222> LOCATION: (39)..(39)
<223> OTHER INFORMATION: Residue No. 39 is optionally modified with an
      amino group.

<400> SEQUENCE: 1

Trp Gln Glu Trp Glu Gln Lys Ile Thr Ala Leu Leu Glu Gln Ala Gln
1               5                   10                  15

Ile Gln Gln Glu Lys Asn Glu Tyr Glu Leu Gln Lys Leu Asp Lys Trp
            20                  25                  30

Ala Ser Leu Trp Glu Trp Phe
        35

<210> SEQ ID NO 2
<211> LENGTH: 7
<212> TYPE: PRT
<213> ORGANISM: Artificial
<220> FEATURE:
<223> OTHER INFORMATION: Peptide sequence was synthetically derived.

<400> SEQUENCE: 2

Asn Glu Tyr Glu Leu Gln Lys
```

```
                              -continued

<210> SEQ ID NO 3
<211> LENGTH: 14
<212> TYPE: PRT
<213> ORGANISM: Artificial
<220> FEATURE:
<223> OTHER INFORMATION: Peptide sequence was synthetically derived.

<400> SEQUENCE: 3

Ile Thr Ala Leu Leu Glu Gln Ala Gln Ile Gln Gln Glu Lys
1               5                   10

<210> SEQ ID NO 4
<211> LENGTH: 7
<212> TYPE: PRT
<213> ORGANISM: Artificial
<220> FEATURE:
<223> OTHER INFORMATION: Peptide sequence was synthetically derived.

<400> SEQUENCE: 4

Trp Gln Glu Trp Glu Gln Lys
1               5

<210> SEQ ID NO 5
<211> LENGTH: 8
<212> TYPE: PRT
<213> ORGANISM: Artificial
<220> FEATURE:
<223> OTHER INFORMATION: Peptide sequence was synthetically derived.
<220> FEATURE:
<221> NAME/KEY: MOD_RES
<222> LOCATION: (8)..(8)
<223> OTHER INFORMATION: Residue No. 8 is modified with an amino group.

<400> SEQUENCE: 5

Trp Ala Ser Leu Trp Glu Trp Phe
1               5
```